(12) United States Patent
Wensel et al.

(10) Patent No.: US 11,976,261 B2
(45) Date of Patent: May 7, 2024

(54) INTEGRATED ALGAL AND CYANOBACTERIAL PROCESS FOR BIOPRODUCT MANUFACTURING

(71) Applicants: Pierre C. Wensel, Mesa, AZ (US); Henri Gerken, Queen Creek, AZ (US)

(72) Inventors: Pierre C. Wensel, Mesa, AZ (US); Henri Gerken, Queen Creek, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 544 days.

(21) Appl. No.: 17/164,641

(22) Filed: Feb. 1, 2021

(65) Prior Publication Data
US 2021/0238519 A1    Aug. 5, 2021

Related U.S. Application Data

(60) Provisional application No. 62/968,469, filed on Jan. 31, 2020.

(51) Int. Cl.
*C12M 1/04* (2006.01)
*C12M 1/00* (2006.01)
*C12M 3/00* (2006.01)

(52) U.S. Cl.
CPC ............ *C12M 21/02* (2013.01); *C12M 23/24* (2013.01); *C12M 23/44* (2013.01); *C12M 23/58* (2013.01); *C12M 29/16* (2013.01)

(58) Field of Classification Search
None
See application file for complete search history.

(56) References Cited

U.S. PATENT DOCUMENTS

| | | | |
|---|---|---|---|
| 6,168,642 B1* | 1/2001 | Valkanas | B09B 3/00 241/24.22 |
| 2008/0014622 A1* | 1/2008 | Federspiel | B01D 71/26 435/182 |

(Continued)

FOREIGN PATENT DOCUMENTS

WO    WO-9219361 A1 * 11/1992 ............. B01D 53/32

OTHER PUBLICATIONS

Magee et al. "The Effect of Biochar Application in Microalgal Culture on the Biomass Yield and Cellular Lipids of Chlorella vulgaris." Proceedings of Chemeca 2013: Challenging tomorrow, Published—2013,870-874. (Year: 2013).*

(Continued)

*Primary Examiner* — William H. Beisner
(74) *Attorney, Agent, or Firm* — Snell & Wilmer L.L.P.

(57) ABSTRACT

A bioproduct manufacturing system is disclosed. The system comprises a hollow-fiber primary membrane gas absorber comprising a shell side and a lumen, wherein the primary membrane gas absorber is configured to receive a carbonate salt-based solvent on the shell side and a gas mixture comprising oxygen, nitrogen, and carbon dioxide in the lumen, at least one runway algal cassette reactor-photobioreactor, and a growth medium circulating between the primary membrane gas absorber and the at least one runway algal cassette reactor-photobioreactor. The at least one runway algal cassette reactor-photobioreactor comprises at least one growth chamber coupled to and in fluid communication with a headspace channel so as to define and interior volume, a first condenser coupled to and in fluid communication with the headspace channel, and a harvest line in fluid communication with the at least one growth chamber and coupled to a filter.

20 Claims, 6 Drawing Sheets

(56) References Cited

U.S. PATENT DOCUMENTS

| | | | | |
|---|---|---|---|---|
| 2009/0126265 | A1* | 5/2009 | Rasmussen | C12M 41/34 47/1.4 |
| 2010/0028976 | A1* | 2/2010 | Hu | C12M 23/02 435/257.1 |
| 2012/0322130 | A1* | 12/2012 | Garcia-Perez | C12P 5/023 435/167 |
| 2013/0319059 | A1 | 12/2013 | Chen et al. | |
| 2014/0106422 | A1* | 4/2014 | Melis | C12N 1/12 435/167 |
| 2015/0024453 | A1* | 1/2015 | Fradette | C12Y 402/01001 435/232 |
| 2015/0099275 | A1* | 4/2015 | Berberoglu | C10G 1/065 422/198 |
| 2015/0136121 | A1* | 5/2015 | Jansen | C07G 1/00 127/55 |
| 2020/0368679 | A1* | 11/2020 | Lefebvre | B01D 53/62 |

OTHER PUBLICATIONS

Yong et al. "In situ layer-by-layerassembledcarbonicanhydrase-coatedhollow fiber membranecontactorforrapid$CO_2$ absorption." Journal of Membrane Science 514 (2016) 556-565. (Year: 2016).*

* cited by examiner

INTEGRATED ALGAL AND CYANOBACTERIAL PROCESS FOR BIOPRODUCT MANUFACTURING

CROSS-REFERENCE TO RELATED APPLICATIONS

This application claims priority to and the benefit of U.S. Provisional Patent Application No. 62/968,469 filed on Jan. 31, 2020 entitled INTEGRATED ALGAL AND CYANOBACTERIAL PROCESS FOR BIOFUEL MANUFACTURING, the disclosure of which is incorporated herein by reference (except for any subject matter disclaimers or disavowals, and except to the extent of any conflict with the disclosure of the present application, in which case the disclosure of the present application shall control).

TECHNICAL FIELD

The present disclosure relates to production of bioproducts, and in particular to use of microalgal and cyanobacterial approaches for bioproduct generation.

BACKGROUND

Prior bioproduct manufacturing systems and methods have suffered from various deficiencies. Commercialization of algal-based processes for biofuels and co-products is constrained upstream during cultivation by low productivity, contamination by invasive species, unsustainable and inefficient supply of nutrients (e.g., nitrogen, sulfur, and phosphorous), inorganic carbon, and water, exposure to environmental factors, and limited available land acreage for inoculum and subsequent large-scale cultures. It is also constrained downstream by costly and inefficient harvesting, cell disruption, product extraction, thermochemical conversion, hydrotreatment, and upgrading.

Conventional processes for solvent-based post-combustion $CO_2$ capture and purification from utility flue gas derived from coal or natural gas-fired boilers utilize absorption and desorption of $CO_2$ in alkanolamines, for example, by using 30 wt % primary monoethanolamine (MEA) or secondary diethanolamine (DEA) liquid solvent in packed bed columns. However, amine absorption of $CO_2$ is expensive. Conventional MEA absorption-desorption processes are disadvantageous for numerous reasons, including (1) high thermal energy requirements (for example, to absorb $CO_2$ gas at 30-50° C. and regenerate at 120-140° C.) (2) the costly, corrosive, and volatile reagents which can result in solvent loss and replenishment that amounts to 10% of the total operating costs and can require costly waste disposal management, (3) high equipment costs, for example, from the absorber/stripper units, and the foaming, flooding, channeling, and entrainment in a process involving the complex interaction of 3 phases (i.e. liquid, gas, solid), (4) high pumping and compression energy requirements, for example, to circulate solvent and gas against gas-liquid pressure drops of columns, and (5) high costs of compressing, cryogenically storing, and transporting the final purified $CO_2$ gas product to be used remotely for algal cultivation.

Conventional processes for algal-based post-combustion $CO_2$ capture are disadvantageous for numerous reasons, including: (1) uneconomic outgassing losses from high-surface area culture vessels (i.e. ponds, PBRs), for example, because of asymmetry between the relatively small volume or scale of culture vessels and the relatively large flue gas flow rates, (2) inability to photosynthetically capture $CO_2$ gas at night in the absence of light, (3) high costs of compression to increase gas partial pressure as a way to increase gas-liquid mass transfer rates for a $CO_2$ gas that is sparingly soluble, for example, at high summer temperatures when sparging or diffusing flue gas directly into a liquid algal culture, (4) premature acidification of algal growth medium which in turn inhibits growth and/or increases risk of contamination, leads to costly pond crashes, and/or necessitates costly preventive contamination-detection equipment and methods, (5) costly insurance and training of personnel for compressed-gas handling, and (6) inaccurate and faulty gas-flow rate metering and/or dissolved $CO_2$ concentration analysis.

Accordingly, improved bioproduct manufacturing systems and methods remain desirable.

BRIEF DESCRIPTION OF THE DRAWINGS

With reference to the following description and accompanying drawings.

Figure 1:
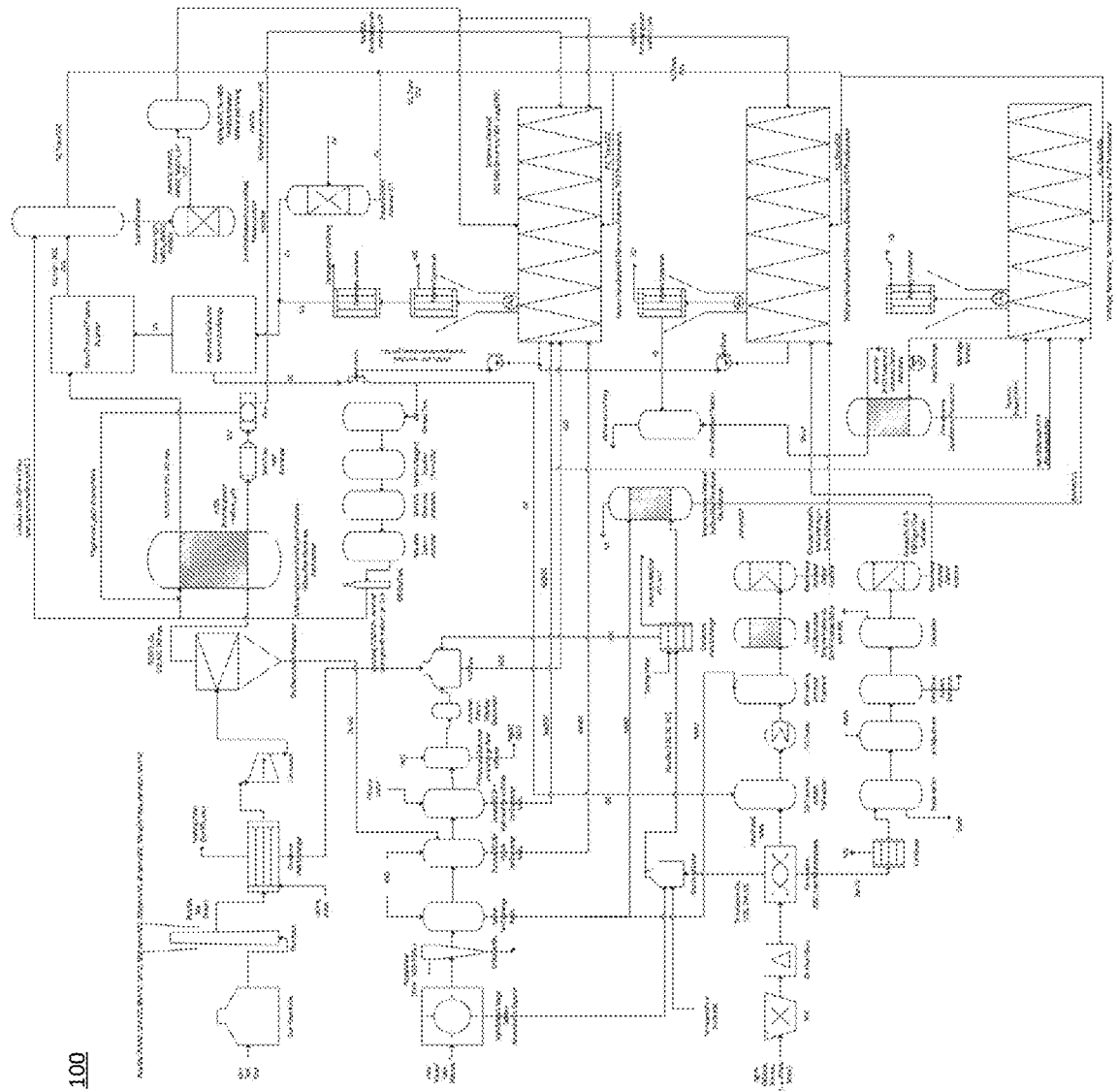
FIG. 1 illustrates an exemplary bioproduct manufacturing system and method in accordance with an exemplary embodiment.

The foregoing drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

SUMMARY

Provided herein is a bioproduct manufacturing system comprising a hollow-fiber primary membrane gas absorber comprising a shell side and a lumen, wherein the primary membrane gas absorber is configured to receive a carbonate salt-based solvent on the shell side and a flue gas in the lumen, at least one runway algal cassette reactor-photobioreactor, and a growth medium circulating between the primary membrane gas absorber and the at least one runway algal cassette reactor-photobioreactor. The at least one runway algal cassette reactor-photobioreactor comprises at least one growth chamber coupled to and in fluid communication with a headspace channel so as to define an interior volume, a first condenser coupled to and in fluid communication with the headspace channel, and a harvest line in fluid communication with the at least one growth chamber and coupled to a filter. In various embodiments, the primary membrane gas absorber is configured to receive the growth medium from the at least one runway algal cassette reactor-photobioreactor in a bicarbonate-depleted state, and the at least one runway algal cassette reactor-photobioreactor is configured to receive the growth medium in a bicarbonate-enriched state.

In various embodiments, the system further comprises carbonic anhydrase enzyme immobilized on a hollow fiber surface of the primary membrane gas absorber. In various embodiments, the system further comprises linear primary amine poly-L-Lysine immobilized on a hollow fiber surface of the primary membrane gas absorber. In various embodiments, a soluble enzyme mimic PNipAm-co-CyclenZn is communicated to the growth medium when it is in a bicarbonate-depleted state.

In various embodiments, the system further comprises a secondary condenser coupled to the headspace channel and configured to condense a volatile terpenoid secreted by organisms disposed in growth chambers. In various embodiments, the system further comprises at least one cassette disposed in the at least one growth chamber. In various embodiments, the system further comprises a vacuum pump in fluid communication with the headspace channel and downstream of the first condenser. In various embodiments, the system further comprises an $N_2$ sparger disposed at a bottom of, and in fluid communication with, the at least one growth chamber. In various embodiments, the system further comprises at least one of a non-thermal plasma reactor, a dielectric barrier discharge reactor, and a soda ash absorber. In various embodiments, the system further comprises at least one of a hydrothermal liquefaction process unit and a hydrotreatment reactor.

In various embodiments, the at least one runway algal cassette reactor-photobioreactor comprises a first RACR-PBR configured to cultivate a filamentous, haloalkaliphilic cyanobacterium, a second RACR-PBR configured to cultivate a filamentous, haloalkaliphilic microalgae, and a third RACR-PBR configured to cultivate a non-haloalkaliphilic microalgae. In various embodiments, the system further comprises a secondary membrane gas absorber. In various embodiments, the at least one runway algal cassette reactor-photobioreactor comprises an elongated shape and is configured to establish a spatial gradient of pH and alkalinity that increases towards a terminal end of the at least one runway algal cassette reactor-photobioreactor.

In various embodiments, the present disclosure provides a bioproduct manufacturing system, comprising a hollow-fiber primary membrane gas absorber comprising a shell side and a lumen, wherein the primary membrane gas absorber is configured to receive a carbonate salt-based solvent on the shell side and a gas mixture of oxygen, nitrogen, and carbon dioxide in the lumen, at least one runway algal cassette reactor-photobioreactor, and the growth medium circulating between the primary membrane gas absorber and the at least one runway algal cassette reactor-photobioreactor, wherein the primary membrane gas absorber is configured to facilitate conversion of carbon dioxide gas disposed in the gas mixture of oxygen, nitrogen, and carbon dioxide into soluble bicarbonate disposed in the growth medium. The at least one runway algal cassette reactor-photobioreactor comprises at least one growth chamber coupled to and in fluid communication with a headspace channel so as to define an interior volume, a first condenser coupled to and in fluid communication with the headspace channel, and a harvest line in fluid communication with the at least one growth chamber and coupled to a filter.

In various embodiments, the bioproduct manufacturing system further comprises a lignocellulosic biomass pathway configured to pre-treat lignocellulosic biomass with torrefaction to produce at least one of biogas, bio-oil, and bio-char, wherein the bio-oil is refined to produce acetate, and wherein the acetate and the organic carbon are communicated to the at least one runway algal cassette reactor-photobioreactor. In various embodiments, the lignocellulosic biomass comprises wheat straw.

In various embodiments, the bioproduct manufacturing system further comprises a waste pathway comprising at least one ion exchange resin, wherein the waste pathway is configured to fractionate wastewater from at least one of food waste and manure to recover nitrogen and phosphorous. In various embodiments, the at least one ion exchange resin comprises at least one of a zeolite ion exchange resin, a Purolite ion exchange resin, and a polymeric ion exchanger impregnated with nanoparticles of hydrated ferric oxide. In various embodiments, the waste pathway further comprises a polystyrene sulfonate-based ion exchange resin.

In various embodiments, the bioproduct manufacturing system further comprises a non-thermal plasma reactor configured to oxidize NOx and SOx pollutants in the flue gas to produce $NO_2$ and $SO_3$ gas, and a soda ash absorber configured to receive $NO_2$ and $SO_3$ gas and to produce $NaHSO_3+CO_2$, wherein the $NaHSO_3+CO_2$ is used to enrich the growth medium.

In various embodiments, the present disclosure provides a bioproduct manufacturing system, comprising a hollow-fiber primary membrane gas absorber comprising a shell side and a lumen, wherein the primary membrane gas absorber is configured to receive a carbonate salt-based solvent on the shell side and a gas mixture of oxygen, nitrogen, and carbon dioxide in the lumen, and wherein carbonic anhydrase enzyme is immobilized on a hollow fiber surface of the primary membrane gas absorber. In various embodiments, the bioproduct manufacturing system further comprises a first RACR-PBR configured to cultivate a filamentous, haloalkaliphilic cyanobacterium, a second RACR-PBR configured to cultivate a filamentous, haloalkaliphilic microalgae, a third RACR-PBR configured to cultivate a non-haloalkaliphilic microalgae, a lignocellulosic biomass pathway configured to produce at least one of biogas, bio-oil, and organic carbon, a waste pathway configured to recover nitrogen and phosphorous from fractionated waste water, at least one of a non-thermal plasma reactor, a dielectric barrier discharge reactor, a soda ash absorber, a hydrothermal liquefaction process unit, and a hydrotreatment reactor, and a growth medium circulating between the primary membrane gas absorber and the at least one runway algal cassette reactor-photobioreactor. In various embodiments, the primary membrane gas absorber is configured to receive the growth medium from the at least one runway algal cassette reactor-photobioreactor in a bicarbonate-depleted state, and the at least one runway algal cassette reactor-photobioreactor is configured to receive the growth medium in a bicarbonate-enriched state.

In various embodiments, the present disclosure provides a photobioreactor, comprising at least one growth chamber coupled to and in fluid communication with a headspace channel so as to define an interior volume, a first condenser coupled to and in fluid communication with the headspace channel, and a harvest line in fluid communication with the at least one growth chamber and coupled to a filter. In various embodiments, the at least one growth chamber comprises an elongated shape and is configured to establish a spatial gradient of pH and alkalinity that increases towards a terminal end of the photobioreactor.

In various embodiments, the present disclosure provides a membrane gas absorber, comprising a hollow-fiber membrane gas absorber comprising a shell side and a lumen, wherein the membrane gas absorber is configured to receive a carbonate salt-based solvent on the shell side and a gas mixture of oxygen, nitrogen, and carbon dioxide in the lumen.

The foregoing features and elements may be combined in various combinations without exclusivity, unless expressly indicated herein otherwise. These features and elements as well as the operation of the disclosed embodiments will become more apparent in light of the following description and accompanying drawings.

DETAILED DESCRIPTION

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from principles of the present disclosure.

For the sake of brevity, conventional techniques for bioproduct manufacturing and use and/or the like may not be described in detail herein. Furthermore, the connecting lines shown in various figures contained herein are intended to represent exemplary functional relationships and/or physical couplings between various elements. It should be noted that many alternative or additional functional relationships or physical connections may be present in an exemplary bioproduct manufacturing system or components or methods thereof.

Principles of the present disclosure contemplate novel systems and methods for bioproduct manufacturing and use. To improve solvent-based and algal-based carbon capture and sequestration, as well as algal-based bioproduct manufacturing, a closed-loop bioproduct manufacturing system involving the integration of, among others, Runway Algal Cassette Remediation Photobioreactor (RACR-PBR), Advanced Oxidation Process (AOP), Anaerobic Digestion (AD), Flue Gas Fractionation (FGF), Effluent Nutrient Recovery (ENR), Lignocellulosic Biomass Fractionation (LBF), and a Membrane Gas Absorber (MGA), are described herein.

With reference to FIG. 1, principles of the present disclosure contemplate a novel, integrated bioproduct manufacturing system to address these aforementioned challenges and offer additional features and advantages. The central themes of an exemplary embodiment are (1) bio-prospecting, genetic modification, and cultivation of appropriate filamentous and/or haloalkaliphilic microalgae and cyanobacteria in novel runway algal cassette reactor-photobioreactors (RACR-PBRs), (2) production and use of a novel membrane gas absorbers (MGAs), and (3) use of the RACP-PBR and MGA in an integrated, closed-loop system for bioproduct manufacturing that includes (a) fractionation of flue gas from coal-fired boilers, (b) fractionation of wastewater, and (c) fractionation of solid agricultural waste.

In various embodiments, the present disclosure provides systems and methods that cultivate a variety of filamentous algae, microalgae, and/or cyanobacteria for use in a novel bioproduct manufacturing system. Cultivation of such algae may occur in one or more RACR-PBRs, as described herein.

Runway Algal Cassette Reactor-Photobioreactor (RACR-PBR)

In one aspect of the present disclosure, a novel algal photobioreactor is provided. The photobioreactor may comprise a runway algal cassette reactor-photobioreactor, or RACR-PBR. The RACR-PBR may be designed specifically for cultivation of filamentous algal strains and/or cyanobacteria. The RACR-PBR may be designed specifically for cultivation of haloalkaliphilic algal strains and/or cyanobacteria, and/or organisms that are tolerant of haloalkaline conditions.

In various embodiments, the structure of the RACR-PBR may support and/or establish spatial and temporal gradients in pH and alkalinity, thereby improving $CO_2$ capture by the bioproduct manufacturing system as described herein. Moreover, the RACR-PBR may (a) facilitate biomass harvesting or transitions between organic carbon and inorganic carbon-based growth media via cost-effective, gravity-assisted drainage of culture, (b) enable easy, cost-effective recovery of volatile product (e.g., $H_2$ and terpenoid) via an enclosed architecture with headspace for removal of humidity and inhibitory photo-evolved $O_2$, (c) enable collection of a pure, volatile terpenoidal biofuel pre-cursor requiring no additional hydrothermal liquefaction-based fractionation, but which can be optionally hydrotreated, for example, with hydrogen gas secreted by diazotrophic cyanobacteria (e.g., by *Oscillatoria* sp. under dark conditions—e.g., at night— during nitrogen-fixation that is temporally separated from photosynthesis to avoid oxygen-inhibition of nitrogenase enzyme, or by *Anabaena* sp. under light conditions—e.g., in the daytime—during nitrogen-fixation that is spatially separated from photosynthesis via heterocystous compartments to avoid oxygen-inhibition of nitrogenase enzyme), (d) enable collection and harvesting of filamentous biomass that is subsequently fractionated into bio-oil, biogas, bio-char, and aqueous solution via hydrothermal liquefaction to produce fuels and other bioproducts, (e) facilitate control of process variables like $N_2$ or $O_2$ gas flow rates, programmable LED light intensity and wavelength for internal and external illumination, temperature, culture volume and/or liquid flow rates and associated levels of C, N, S, P nutrient, alkalinity, and/or pH, and/or (f) reduce risk of contamination via sparging of pure $N_2$ derived from flue gas fractionation or other means via the enclosed nature of the roofed headspace.

The RACR-PBRs may be elongated, plug flow-like photobioreactors with segmented, cascading, modules or "cassettes" divided by nylon mesh walls and inter-connecting short pipes which allow only the alkaline growth medium to pass through downward from one module to the next. In an alternative embodiment, the RACR-PBR comprises a monolithic elongated PBR (either vertical flat-panel or vertical bag configuration) segmented into individual compartments that are separated by a mesh wall allowing only the growth medium to pass through. In various embodiments, the growth medium may comprise bicarbonate salt-based solvent.

In various embodiments, modularity of a RACR-PBR may facilitate establishment of a spatial gradient in pH and alkalinity, where bicarbonate-enriched, pH 9 growth medium that is generated by the later-described MGA is delivered at the top starting module, while spent carbonate/hydroxyl-enriched, pH 11.5 spent medium is withdrawn and pumped from the bottom terminal module to the MGA for continuous $CO_2$ capture in a closed-loop manner. The non-turbulent, mildly aerated, liquid flow and segmented modularity may allow such a spatial gradient in pH and alkalinity. In various embodiments, with adequate module dimensions (i.e. thin light path), modularity of the RACR-PBR may also allow sufficient penetrative light transfer (i.e. scattering and absorption), momentum transfer (mixing), heat transfer (i.e. cooling water coil), and mass transfer (i.e. removal of dissolved oxygen during phototrophic stage, injection of $N_2$ during diazotrophic stage) to facilitate growth. In various embodiments, modularity of the RACR-PBR may allow it to accommodate any configuration or shape of growth chamber (e.g., a less expensive plastic bag, a more expensive acrylic flat-panel, etc.).

Additionally, cultivation of algae and/or cyanobacterium in semicontinuous/batch mode may facilitate establishment of a temporal gradient in pH and alkalinity in the RACR-PBR. The semicontinuous/batch mode may cause spent alkaline growth medium used during the day for phototrophic growth to be completely withdrawn at nightfall and replaced with previously tank-stored growth medium containing organic carbon derived from lignocellulosic biomass, as described later. During night in the absence of light for photosynthesis, the collected spent, carbonate-enriched alkaline inorganic carbon growth medium containing $CO_3^{2-}$ and OH-alkalinity may be used as a cheap solvent to capture $CO_2$ in the MGA (hereinafter described) and to generate new bicarbonate-enriched growth medium which is temporarily stored in a tank and later used the following morning. At the same time at night, the organic carbon-enriched growth medium is used to consume dissolved oxygen and induce respiratory oxidative phosphorylation to boost productivity. At daybreak, the spent organic carbon medium may be drained from the RACR-PBR and replaced with newly generated bicarbonate-enriched growth medium that was stored at night in a tank to allow for phototrophic growth on bicarbonate.

In various embodiments, $N_2$ gas may be introduced into the RACR-PBR to facilitate growth of algae and/or cyanobacteria. In various embodiments, the $N_2$ gas is sparged into culture via an $N_2$ sparger—a perforated pipe disposed at the bottom of one or more growth chambers of the RACR-PBR. Such a perforated pipe may comprise a PVC pipe perforated with relatively 1 mm large-diameter holes and running along the bottom axial length of the RACR-PBR modules for low-pressure, high-momentum agitation and mixing. In various embodiments, the $N_2$ gas is compressed and molecularly diffused via a hollow-fiber membrane running along the bottom axial length of the RACR-PBR for bubble-less gas-liquid mass transfer. In various embodiments, the $N_2$ gas comprises relatively pure $N_2$ gas released from the soda ash absorber of the later-described gas mixture of oxygen, nitrogen, and carbon dioxide fractionation segment combined and compressed with additional pure $N_2$ generated from integrated pressure-swing adsorber hereinafter described.

In various embodiments, the RACR-PBR comprises a headspace architecture. The headspace architecture may be coupled to the walls of the elongated growth chamber(s) via hinges to allow opening and closing of the headspace for maintenance, cleaning, and/or harvesting. Harvesting of cyanobacteria or algae from an individual module may occur by opening a bottom drain valve configured to prevent plugging by decaying biomass and contamination via positive pressure. Opening the bottom drain valve may allow the culture of algae, cyanobacteria, growth media, and/or other materials to be collected by gravity and filtered, for example, through a nylon mesh bag. In various embodiments, after filtration, wet biomass may be collected, for example, by scraping off the filter, to be subsequently lyophilized, hydrothermally liquefied (HTL), and/or for other treatment(s) (disruption, extraction, pulsed electric field (PEF), etc.). In various embodiments, the resulting permeate may be stored in a tank and used for later cultivation or other applications.

In various embodiments, the RACR-PBR may be illuminated both with external and internal light sources. External light sources include, but are not limited to, (a) artificial polychromatic light sources, such as fluorescent fixtures, (b) natural sunlight, the incident the angle of which varies by weather cloud index, calendar day, calendar season, and geographical location, and (c) monochromatic light sources, such as strips of red LEDs whose average light intensity can be either set via voltage dimmer or via pulse field modulation for "flashing-light effect" to synchronize algal dark and light photosynthetic reactions and enhance photosynthetic efficiency. Internal light sources include, but are not limited to, (a) monochromatic or polychromatic waterproof LED, and (b) Na-plasma lamp. In various embodiments, a lathed acrylic light guide may run along bottom axial length of the module in parallel to cooling coils, $N_2$ sparger, and/or $N_2$-hollow-fiber.

Figure 2:
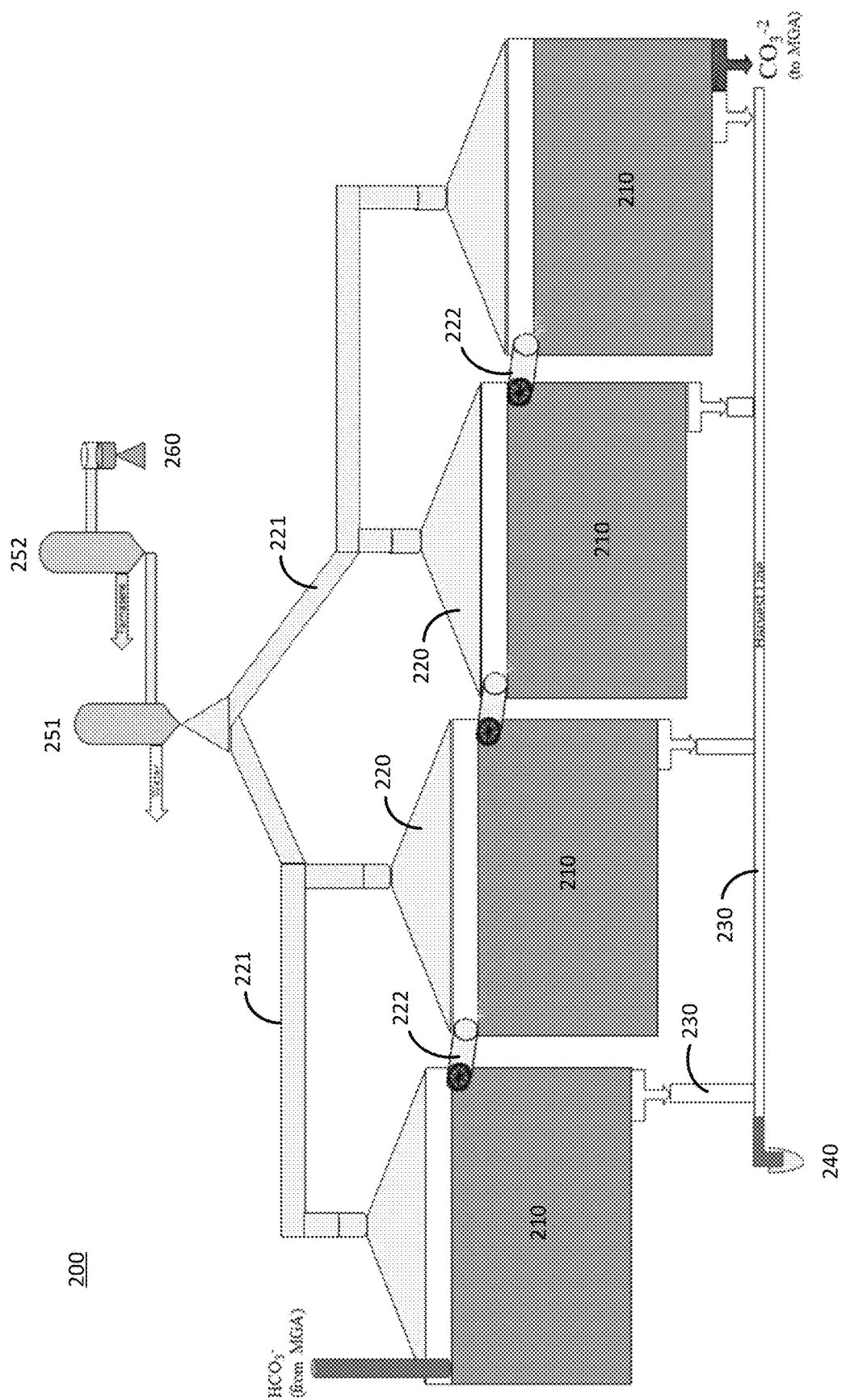
FIG. 2 illustrates a runway algal cassette reactor-photobioreactor (RACR-PBR) in accordance with various embodiments.

In various embodiments and with reference to FIG. 2, a RACR-PBR 200 comprises one or more elongated growth chambers 210 configured to cultivate filamentous algae and/or cyanobacteria. Each growth chamber 210 may comprise an interior volume configured to receive filamentous algae and algal growth medium. Each growth chamber 210 may further comprise a cassette disposed in the interior volume of growth chamber 210. The cassette may provide a surface area for algal growth within growth chamber 210. The cassette may be optionally removable from growth chamber 210. In various embodiments, the cassette comprises a mesh basket. In various embodiments, the cassette may comprise a 74 micron stainless steel mesh basket. However, the cassette may comprise any structure capable of providing a growth surface area to filamentous algae, while also allowing water, fluid, and/or growth medium to flow through RACR-PBR 200.

In various embodiments, RACR-PBR 200 comprises a plurality of growth chambers 210 coupled in series via one or more flow-through channels 222. The plurality of growth chambers 210 may be in fluid communication with one another and arranged in series. In such embodiments, RACR-PBR 200 may be configured such that water, growth medium, or other fluid may be communicated in series from a first growth chamber, serially through the plurality of growth chambers to a terminal growth chamber. In various embodiments, RACR-PBR 200 comprises a single, elongated growth chamber 210 configured to receive water, growth medium, or other fluid at a first end, which is then communicated along the length of the single, elongated growth chamber to the second, terminal end.

Without being bound by theory, the elongated nature of the RACR-PBR growth chamber(s) 210 as described herein may facilitate the establishment of spatial and temporal gradients in pH and alkalinity to occur along the length of the RACR-PBR growth chamber(s) 210. In various embodiments, collection of higher pH spent growth medium from a terminal end of the RACR-PBR growth chamber(s) 210 may provide efficacy and efficiency benefits for use in the bioproduct manufacturing systems as described herein.

RACR-PBR 200 may further comprise an enclosed headspace 220 disposed above and/or coupled to the one or more growth chambers 210. Enclosed headspace 220 may be configured to create an enclosed or substantially enclosed volume above the one or more growth chambers 210. Enclosed headspace 220 may protect filamentous algae disposed therein from ambient contaminants. Enclosed headspace 220 may provide one or more headspace channels 221 through which gases, volatile compounds, and/or other fluids may be communicated to other portions of RACR-PBR 200.

In various embodiments, RACR-PBR 200 further comprises one or more harvest lines 230. Harvest line 230 may be configured for gravity-assisted drainage of algae, fluids, and/or other materials in growth chambers 210. In various embodiments, harvest line 230 may consolidate drainage materials from a plurality of growth chambers 210. In various embodiments, the RACR-PBR 200 may comprise a separate harvest line 230 for each growth chamber 210. In some embodiments, harvest line 230 may communicate fluid and/or biomass disposed in growth chambers 210 to a filter 240. Filter 240 may be configured to separate algal biomass from spent growth medium. In various embodiments, filter 240 comprises a mesh sock screen.

In various embodiments, RACR-PBR 200 further comprises one or more condensers in fluid communication with the headspace channels 221. For example, RACR-PBR 200 may comprise a first condenser 251 configured to condense water from the fluid that evolves and is communicated through headspace channels 221. RACR-PBR 200 may further comprise a second condenser 252 configured to condense one or more volatile compounds that evolves and is communicated through headspace channels 221. For example, in various embodiments, second condenser 252 is configured to condense a terpenoid and/or hydrocarbon secreted by organisms disposed in growth chambers 210, as more fully described herein. In various embodiments, the terpenoid hydrocarbon comprises farnesene. In various embodiments, the terpenoid is subsequently hydrotreated with hydrogen gas to produce an alkane hydrocarbon.

In various embodiments, RACR-PBR 200 further comprises a vacuum pump 260 in fluid communication with headspace channel 221. In various embodiments, vacuum pump 260 is disposed downstream of first condenser 251 and/or second condenser 252. Vacuum pump 260 may be configured to sparge various gases, for example, nitrogen or oxygen, from RACR-PBR 200 and, more specifically, from enclosed headspace 220. In various embodiments, by the combined temperature gradient created by condensers 251, 252, pressure gradient created by the sparging of $N_2$ into the bottom of the PBR culture and vacuum pump 260 downstream of said condensers, accumulated humid gas may be evacuated out of enclosed headspace 220, through headspace channel 221, and towards the condensers 251, 252.

In various embodiments, cultivation of filamentous and/or haloalkaliphilic strains in the RACR-PBRs of the present disclosure may provide various advantages for use in bioproduct manufacturing systems, as described herein. For example, filamentous morphology of algal strains in the RACR-PBR may (a) help resist contamination by undesirable organisms which thereby reduce or eliminate costs associated with pond-crashes and contamination detection, and (b) reduce or eliminate the capital and operating costs associated with membrane filtration, centrifugation, flocculation, or other conventional harvesting methods otherwise used for non-filamentous algae when continually pumping and recycling spent alkaline growth medium solvent within the bioproduct manufacturing system. However, the use of various prokaryotic and eukaryotic organisms, including algae and cyanobacteria, are within the scope of this disclosure.

In various embodiments, the RACR-PBR described herein is configured for cultivation of various organisms, for example, algae and cyanobacteria. In various embodiments, a mutant, filamentous, haloalkaliphilic, diazotrophic, heterotrophic-phototrophic cyanobacterium Soap Lake isolate *Anabaena* sp. 200-13D is cultivated. In various embodiments, the cyanobacteria may produce significant quantities of a pure, secreted, volatile terpenoid hydrocarbon and/or a sucrose-rich biomass that upon harvesting can be fermented to bioethanol or can be hydrothermally liquefied and refined as a biofuel. Compared to other biofuels and biofuel precursors generated by algal biomass, farnesene or other terpenoids collected via condensation of enclosed headspace of the RACR-PBR, does not require expensive cellular disruption, product extraction, high-temperature processing like hydrothermal liquefaction or any other downstream catalytic hydrotreatment or biorefining. In various embodiments, cyanobacterial terpenoid production may be enabled via genetic modifications that facilitate high uptake of inorganic carbon bicarbonate during the day, high uptake of organic carbon xylose and glucose during the night, and high carbon flux away from production of anatoxins and instead towards farnesene and/or other terpenoids. Such genetic modification may include, for example: (a) introduction of codon-optimized Norway spruce farnesene synthase (FaS) gene, (b) introduction of *E. coli* xylose isomerase (xylA) and xylulokinase (xylB) genes, (c) introduction of the bicyclic 3-hydroxypropionate $CO_2$ fixation pathway (for example, as an additional $CO_2$ fixation pathway using bicarbonate precursor and/or as a photorespiratory bypass of the RubsiCo oxygenation reaction, which may re-channel photorespiration products to pyruvate for terpenoid biosynthesis), and/or (d) deletion of anatoxin synthetase (anaA-anaG) gene cluster via CRISPR-CPf1 (for example, to increase carbon flux towards terpenoid production and/or to render biomass less toxic and/or more edible). However, various haloalkaliphilic cyanobacteria and/or other terpenoid hydrocarbon-producing organisms are within the scope of this disclosure.

In various embodiments, filamentous, diazotrophic, haloalkaliphilic, *Oscillatoria* sp. 200-9E Soap Lake isolate is cultivated in the RACR-PBR. This haloalkaliphilic algae may be cultivated for production of $H_2$ gas and biomass in the RACR-PBR. The $H_2$ may be used in the bioproduct manufacturing system described herein to hydrogenate biooil yielded from the hydrothermal liquefaction of wet microalgal biomass and/or to hydrogenate the secreted terpenoid, converting it to alkane, which may be a more readily adopted biofuel. Without being bound by theory, high $H_2$ production by the filamentous, non-heterocystous *Oscillatoria* sp. 200-9E may be enabled in aerobic conditions by a nitrogenase activity that is induced via the temporal separation between $N_2$-fixation from photosynthesis and by its lack of a hydrogenase uptake activity.

In various embodiments, oleaginous, freshwater, non-haloalkaliphilic, phototrophic microalgae are cultivated in the RACR-PBR. In such embodiments, ammonium bicarbonate (NH4HCO3) derived from the integrated MGA (hereinafter described) may simultaneously supply a C and N source to the RACR-PBR. In such embodiments, phosphate buffer (NaH2 PO4/Na2 HPO4) derived from an integrated wastewater fractionating ion-exchanger column (hereinafter described) may simultaneously serve as buffer and P source to the RACR-PBR. In various embodiments, consumption of ammonia and/or the phosphate buffering may limit an otherwise inhibitory pH increase and associated increase in ammonia volatilization that ensues after phototrophic consumption of bicarbonate. In various embodiments, the microalgae's wet biomass may be treated with hydrothermal liquefaction (HTL) to produce a bio-char. This bio-char may be treated and subsequently used as activated carbon for on-site adsorption processes to de-colorize hydrolysate and acetate solutions from the processing of solid agricultural lignocellulosic waste, thereby reclaiming it within the bioproduct manufacturing systems described herein. For example, the bio-char may be processed and/or pre-treated with ozone and aqueous ammonia at about 42° C. for about 12 hours; the bio-char may be hydrolyzed enzymatically to produce organic carbon and/or detoxified with activated carbon to remove growth inhibitors including but not limited to furans.

Membrane Gas Absorber (MGA)

In one aspect of the disclosure, a primary membrane gas absorber (MGA) is provided herein. The primary MGA comprises a hollow-fiber MGA. In various embodiments, the primary MGA may comprise a highly porous, non-selective, polymeric, and/or hydrophobic hollow fiber membrane. In various embodiments, the hollow-fiber membrane may be configured as a contacting barrier between a gas mixture of oxygen, nitrogen, and carbon dioxide and one or more aqueous solvent streams. In various embodiments, the gas mixture of oxygen, nitrogen, and carbon dioxide is produced by a coal-fired and/or gas-fired burner, i.e., a flue gas, which is subsequently processed by a sorbent system used to pre-concentrate carbon dioxide. In various embodiments, the primary MGA may allow only carbon dioxide to diffuse across and into the absorbing aqueous solvent streams.

In various embodiments, the primary MGA receives spent growth medium from one or more RACR-PBRs on a shell-side of the primary MGA, rather than in a lumen of the primary MGA. In various embodiments, the primary MGA is configured to increase carbon dioxide capture with a hydrogel lumen wall. Use of a primary MGA in the bioproduct manufacturing systems disclosed herein may have various benefits including, without limitation: (a) increased gas-liquid interfacial contact surface area per unit volume for mass transfer, which may result in smaller, more compact equipment or footprint of the primary MGA by as much as 10-20×, (b) decreased membrane thicknesses and smaller molecular transport distances, which may result in higher $CO_2$ volumetric mass transfer coefficients, (c) distinct separation of both phases, which may allow extension of operating window and more flexible, independent control of temperature, pressure, and flow rate of liquid and gas phases without hydrodynamic limitations of flooding or channeling, (d) modularity for easy linear scale-up; (e) decreased cost of primary MGA materials; (f) absorption of carbon dioxide with a higher-surface tension, cost-effective Na2 $CO_3$ solvent that is both cost-effective to purchase and cost-effective to regenerate via co-located filamentous, halo-alkaliphilic algal culture, as described herein; (g) avoidance of low gas and high liquid flow rates and optimized flowrate ratios; and (h) simultaneous decrease in pore wetting and increase in kinetic reaction rates via immobilized catalytic films on primary MGA fibers, as described herein.

In various embodiments, the primary MGA comprises a solvent that is capable of physical absorption of $CO_2$, as well as chemical absorption of $CO_2$. For example, the primary MGA may comprise a carbonate salt-based solvent such as, for example, $K_2 CO_3$ or $Na_2 CO_3$. In various embodiments, such a carbonate salt-based solvent is sourced from recycled growth medium as disclosed herein. Such a carbonate salt-based solvent may buffer solution in the pH range 9-11 to enable OH— in its direct nucleophilic attack $CO_2$ to produce bicarbonate according to the following Equation 1:

$$CO_2(aq)+OH^-\rightarrow HCO_3^- \text{ and } CO_3^{2-}+CO_2+H_2O\rightarrow 2HCO_3^-.$$

In various embodiments, the carbonate salt-based solvent disclosed herein may provide various benefits including, for example, lower cost for equivalent $CO_2$ absorption capacity, higher surface tension, non-volatility, non-toxicity, lower-corrosivity to equipment, chemical inertness with regards to thermally-induced oxidation and/or polymerization-driven degradation, biocompatibility, and/or lower operation energy requirements. In various embodiments, the carbonate salt-based solvent disclosed herein may enable the primary MGA to convert $CO_2$ from a gas mixture of oxygen, nitrogen, and carbon dioxide into bicarbonate. Such bicarbonate may offer advantages over purified $CO_2$, such as, for example, as a more soluble, transportable, and storable source of inorganic carbon. Such bicarbonate may further be used by photobioreactors and for bioproduct manufacturing systems, as disclosed herein.

In various embodiments, the gas mixture fed on the shell side of the MGA is dehumidified and/or compressed air. This air may have been processed via swing-based sorbent technology (e.g., a temperature-swing, pressure-swing, moisture-swing, and/or electrical-swing) to pre-concentrate $CO_2$ and/or raise its partial pressure for more efficient MGA operation. In various embodiments, the temperature swing and/or electrical swing technology involves tandem hollow-fiber sorbent beds comprised of mesoporous SiC that is functionalized with polyethylimine or 13× zeolite. In such embodiments, compressed, dehumidified air is blown over the shell-side of the hollow-fiber sorbent material. In such embodiments, the $CO_2$ in the air mixture is adsorbed at cold temperature (e.g., at about 30° C.+/−15° C.) and desorbed at high temperature (i.e. 80° C.+/−15° C.). This heat may be provided via direct, electrical heating by copper wires at each end of the bed, by steam-heating by steam that is pumped through hollow-fiber lumen to heat the hollow-fiber matrix, and/or by any other suitable source of heat.

In various embodiments, the primary MGA may comprise polypropylene. In various embodiments, the primary MGA may comprise polytetrafluoroethylene (PTFE), polyether-ether-ketone (PEEK), and/or another porous, non-selective, polymeric, and/or hydrophobic material. However, the primary MGA as disclosed herein may comprise any material configured to create a chemical potential gradient across the primary MGA based on the mass transfer driving force or concentration difference between $CO_2$ in a gas mixture of oxygen, nitrogen, and carbon dioxide and $CO_2$ in liquid solvent so as to enable separation of $CO_2$ from other gas mixtures of oxygen, nitrogen, and carbon dioxide constituents. In various embodiments, the primary MGA comprises a non-hydrophobic material that facilitates transport of $CO_2$ and $HCO_3$— ions via fixed, sterically-hindered amine carriers.

In various embodiments, the primary MGA comprises a hollow-fiber membrane of about 200 to about 300 micrometers in diameter. The primary MGA may comprise a hollow-fiber membrane of about 150 to about 1000 micrometers in diameter. However, the primary MGA may comprise a hollow-fiber membrane having any diameter suitable for use in the primary MGA as described herein.

In various embodiments, the primary MGA is configured to increase the kinetic reaction rate and/or decrease thermodynamic heat of absorption/desorption via use of one or more catalysts. Stated differently, the MGA may use recycled, waste, alkaline, carbonate-enriched, non-thermally regenerated spent growth medium derived from alkaliphilic algal or cyanobacterial culture as a $CO_2$-capture absorption solvent instead of conventional amine solvent. The MGA may also comprise carbonic anhydrase to catalyze the hydration of $CO_2$ into aqueous bicarbonate so as to increase reaction rate kinetics without necessitating thermal energy inputs (for example, as required with conventional hot potassium carbonate or hot-potash $CO_2$-capture processes). In various embodiments, the primary MGA comprises a halo-alkali-tolerant carbonic anhydrase (CA) enzyme and/or linear primary amine poly-L-Lysine. In various embodiments, the primary MGA comprises synthetic enzyme mimic PNipAm-co-CyclenZn. In various embodiments, the MGA comprises linear primary amine poly-L-Lysine fused to said carbonic anhydrase enzyme. In various embodiments, the system further comprises carbonic anhydrase enzyme and fused linear primary amine poly-L-Lysine that are immobilized on silica or calcium carbonate particles. In various embodiments, the carbonic anhydrase further exhibits enhanced retention of activity and stability when exposed to high temperatures (i.e >60° C.), high pH (i.e. >9), high alkalinity (>0.5M $Na_2CO_3$), high amine concentration (>0.2M Monoethanolamine (MEA)).

In various embodiments, the CA enzyme is manufactured via genetic immobilization on diatom silica frustule and/or coccolithophore calcium carbonate coccoliths. Diatom-based immobilization for enzyme manufacture may provide various advantages over existing enzyme manufacturing methods, for example: (1) the enzyme to be immobilized may not need to be purified, (2) enzyme manufacture may be more cost-effective, environmentally benign, and/or sustainable, since growth of photosynthetic diatoms requires only sunlight, water, and cheap mineral salts, (3) immobilization may proceed under optimal conditions for protein stability and/or avoid the need to use conventional, toxic, or expensive solvents and cross-linkers, (4) diatom silica may be a desirable matrix for enzyme immobilization due to its high-effective diffusivity and hierarchical nano- to microporous structure, which may exhibit high mechanical stability, mass transfer, and resistance to elevated temperatures, high salt concentrations, and/or acidic conditions, (5) the negative charge of natural biosilica may attract positively charged substrate and repel negatively charged product, resulting in faster kinetics and less product inhibition, (6) immobilization on diatom silica may enhance enzymatic stability, (7) recovery of immobilized enzyme may be achieved via simple centrifugation, membrane filtration, and/or magnetism, should the diatom be cultivated in high levels of iron ions that can ultimately incorporated into the silica frustule as well. In various embodiments, the CA enzyme and/or linear primary amine poly-L-Lysine is disposed as a gas/liquid solvent interface on the surface of the hollow-fiber membrane as disclosed herein. In various embodiments, and as further described below, the CA enzyme and/or linear primary amine poly-L-Lysine may be immobilized on hollow-fiber membrane surface as a non-volatile carbonate-solvent rate activator to help capture and react with $CO_2$ and as a polyelectrolyte layer in layer-by-layer (LbL) immobilization, as it promotes electrostatic interaction between negatively-charged and positively-charged surface ions.

In various embodiments, spent growth medium comprises the carbonate salt-based solvent as described herein. In various embodiments, the spent growth medium is communicated to the shell side of the primary MGA flowed down by gravity and pump flow through a porous pH/ionic-strength-responsive cationic hydrogel as described herein. In various embodiments, the spent growth medium may be injected with a soluble enzyme mimic prior to being communicated to the primary MGA. Such an enzyme mimic may be configured to increase CA enzyme loading and, therefore, bicarbonate conversion. In various embodiments, the soluble enzyme mimic comprises PNipAm-co-CyclenZn.

In various embodiments, the hydrogel is disposed on the shell side of the hollow-fiber membrane. In various embodiments, the hydrogel may buttress the thin catalytic film on the shell-side of the hollow-fiber membrane and/or prevent its disintegration at high alkaline solvent convective pump/gravity flow rates. In various embodiments, because the cationic hydrogel is pH-ionic strength-responsive, there will be a gradient in porosity throughout the hydrogel. In various embodiments, the hydrogel is configured such that its pores open where high-salinity, high-pH solvent enters the primary MGA, and its pores close where dissolved $CO_2$ acidifies the gas-liquid interface, creating a gradient in porosity which helps further limit undesirable pore-wetting of the membrane that otherwise limits mass transfer.

Figure 3:
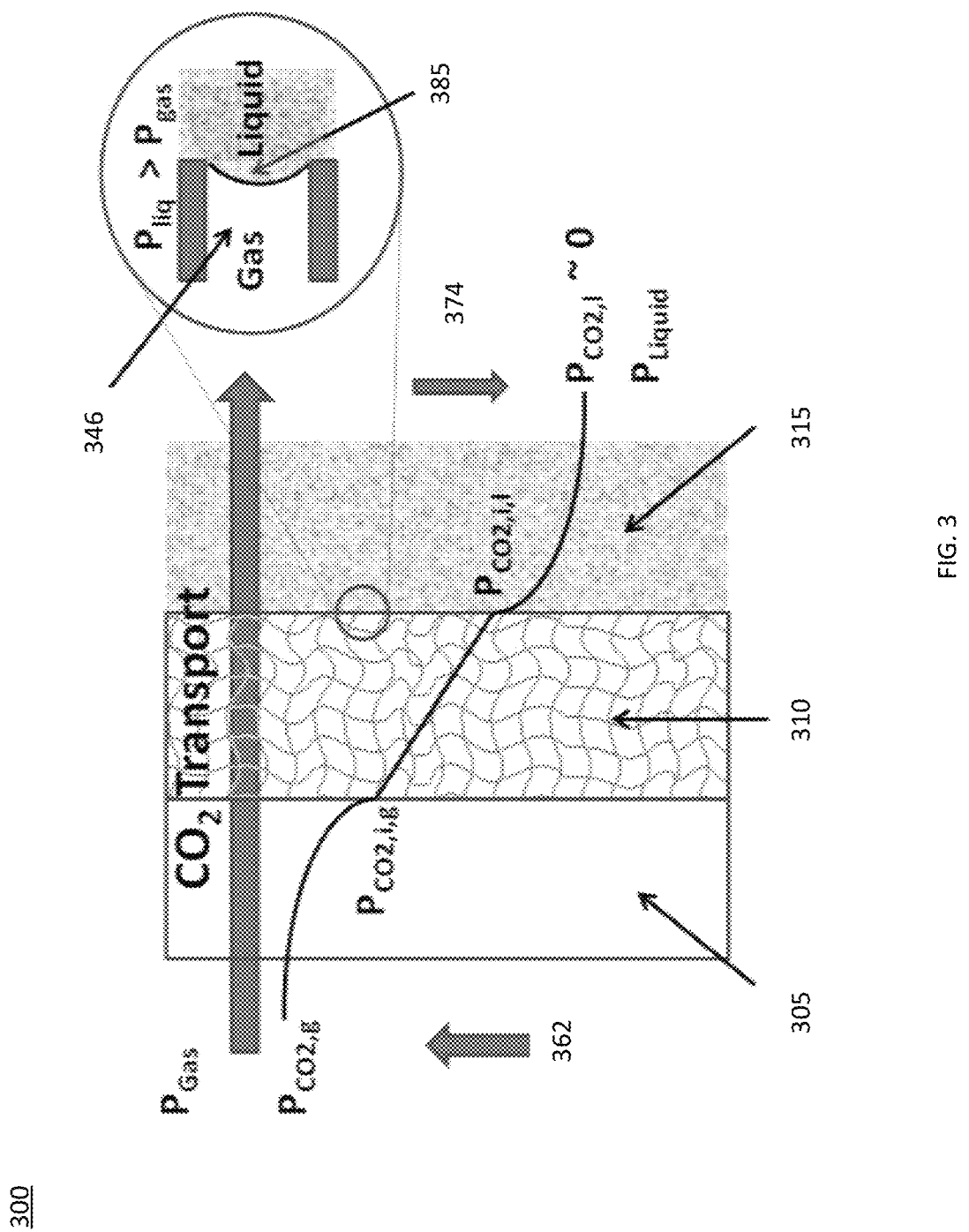
FIG. 3 illustrates a partial view of a primary membrane gas absorber (MGA) and a transport process at a primary MGA pore in accordance with an exemplary embodiment.

With reference now to FIG. 3, a portion of a primary MGA 300 is illustrated, as well as a carbon dioxide transport process through such a primary MGA pore. Primary MGA 300 may comprise one or more hollow-fiber membranes 310 disposed between a gas-side boundary layer 305 and a liquid-side boundary layer 315. A gas mixture of oxygen, nitrogen, and carbon dioxide 362 (for example, flue gas from a coal-fired boiler) containing carbon dioxide may be disposed and/or circulated through gas-side boundary layer 305, while a carbonate salt-based solvent 374, as described herein, is disposed and/or circulated through liquid-side boundary layer 315. In various embodiments, liquid-side boundary layer 315 is disposed on a shell side of hollow-fiber membrane 310 of primary MGA 300. In various embodiments, carbonate salt-based solvent 374 is continuously circulated in a closed loop on liquid-side boundary layer 315 of MGA 300.

A pore 346 of primary MGA 300 is illustrated in the expanded portion of FIG. 3. As more fully described herein, carbon dioxide present in the gas phase in gas mixture of oxygen, nitrogen, and carbon dioxide 362 is transported through hollow-fiber membrane 310 and to pore 346 of primary MGA 300. At the gas-liquid interface between carbonate salt-based solvent 374 and hollow-fiber membrane 310, a catalytic film 385 is disposed. Catalytic film 385 may facilitate the transport and/or capture of carbon dioxide into carbonate salt-based solvent 374 as described herein.

In various embodiments, growth medium may be circulated between the primary MGA and one or more RACR-PBRs in a closed loop. During this closed loop circulation, the alkaline, spent growth medium may be separated from the filamentous, halo-alkaline-tolerant cyanobacteria culture inside the elongated, plug-flow like RACR-PBR by pumping it, and or allowing it to be gravity fed, out through a porous mesh barrier on the terminal end of the RACR-PBR. In various embodiments, the pH is higher at the terminal end if a pH and alkalinity gradient is established or if a temporal gradient is established. In one exemplary embodiment, a culture, which may be supplemented with nitrate or urea salts as nitrogen source, can be grown in batch mode from pH 9 until pH 11.50 is reached, at which point spent growth medium is pumped out, oxidized, and sent to the primary MGA for $CO_2$ capture.

In various embodiments, the liquid medium is then oxidized by an Advanced Oxidation Process (AOP) process involving treatment via ozonation, hydrogen peroxide ($H_2O_2$) UV/$TiO_2$-irradiation, activated carbon adsorption, and/or membrane filtration to remove and destroy biofouling organics, microbes, and viruses. The cleaned liquid growth medium, which may be referred to herein as a carbonate salt-based solvent, may then be injected with a soluble enzyme mimic PNipAm-co-CyclenZn before the solvent enters the shell-side of the MGA at the top. Inside the MGA, the solvent and mimic may flow down by gravity and/or pump flow through a porous and protective pH/ionic-strength-responsive cationic hydrogel counter-currently against a gas mixture of oxygen, nitrogen, and carbon dioxide (for example, flue gas from a coal-fired boiler) that has been dehumidified, cooled, de-ashed, and/or compressed into the lumen of hydrophobic polypropylene hollow-fibers of the MGA through which it flows. In various embodiments, the porous gel may buttress a thin CA-poly-L-Lysine nanoparticle film on the shell-side of the hollow-fibers and/or may prevent disintegration of the film at high solvent flow rates. Without being bound by theory, because the cationic hydrogel is pH-ionic strength-responsive, there may be a gradient in porosity throughout the hydrogel. The gradient created by the hydrogel's pH/ionic-strength swelling response is such that the immediate hollow-fiber membrane/hydrogel interface region may have smaller pores (allowing entry of acidifying $CO_2$ and preventing exit of liquid alkaline solvent and membrane pore wetting) compared to the interior of the hydrogel having larger pores allowing higher convective bulk liquid flow to more quickly evacuate bicarbonate product solution out.

In various embodiments, the $CO_2$ will then travel radially across the primary MGA to separate from other insoluble flue-gas components (i.e. $N_2$, $O_2$, NOx, SOx, Hg0) while traveling in the axial direction of the lumen, and finally will traverse the porous, hydrophobic, hollow-fiber membrane to reach the gas-liquid interface's thin CA-poly-L-Lysine-nanoparticle film via enzyme-facilitated transport.

In various embodiments, this film is a series of adsorbed poly-electrolytic layers with alternating electrostatic charges containing exoskeletons of dead diatom and coccolithophore algae composed of silica and calcium carbonate, respectively, which were genetically transformed to immobilize the amino group-containing poly-L-Lysine and the recombinant Zinc-dependent enzyme alpha-carbonic anhydrase (CA). In various embodiments, it is at this film that the traversed $CO_2$ gas dissolves and is catalytically converted or "hydrated" to more soluble, transportable, and storable bicarbonate. The negatively-charged silica immobilization support may help repel away the inhibitory bicarbonate ion and move it towards the bulk liquid solvent/enzyme mimic flowing on the shell side. Any dissolved $CO_2$ that did not react with CA or the amino group of poly-L-Lysine may be converted by the enzyme mimic dissolved in the alkaline solvent flowing down by gravity through the shell-side of the MGA. All soluble bicarbonate product-enriched solution may then be quickly evacuated out of the MGA.

In various embodiments, the temperature of this product bicarbonate solution is raised to at least about 33° C. (wherein about means+/−2° C.) via a condenser-heat exchanger to precipitate out and recover the synthetic enzyme mimic, which is recovered by membrane cross-flow filtration and pumped back and injected into the relatively cooler, high pH alkaline solvent at the top of the primary MGA.

As a filtration permeate, the bicarbonate product solution may then be pumped to the inlet end of a RACR-PBR where the pH may be relatively lower (for example, if a spatial gradient has been established). In various embodiments, the bicarbonate product solution may be stored in a tank and/or used later in time. This closed loop process may be used as cost-effective, soluble source of inorganic carbon for filamentous, diazotrophic, phototrophic, haloalkaline-tolerant cyanobacteria (i.e., *Anabaena* sp. to produce terpenoids and *Oscillatoria* sp. to produce $H_2$, along with biomass). During the day, the cyanobacteria may consume bicarbonate, and nitrate (nitrite may also be consumed or converted to nitrate by cyanobacteria) as it grows photosynthetically to produce biomass or secreted hydrocarbons, and in turn increase pH and increase alkalinity of growth medium that is recycled back to MGA as solvent as mentioned, simultaneously creating a pH-gradient in the elongated RACR-PBR.

Production of a CA-Immobilized Film

In one aspect of the disclosure, method of producing a film bearing immobilized carbonic anhydrase (CA) for use in a primary MGA, as disclosed herein, is provided. The method may comprise expression of functional, halo-alkali-tolerant CA and/or an evolved amine-tolerant CA from various microorganisms. The method may comprise a rapid layer-by-layer (LbL) technique involving fabrication of a thin, multi-layer film.

In various embodiments, the film is about 0.3 µm-thick (wherein about meant+/−0.1 µm); however, the film may comprise a thickness of between about 0.05 and about 1 or any other thickness suitable for use in the primary MGA. In various embodiments, the film comprises 4 layers; however, the film may comprise 2, 3, 5, or more layers, as are suitable for use in the primary MGA.

In various embodiments, the film is produced via adsorption of alternating charged polyelectrolyte layers. For example, the alternating layers may comprise positively-charged poly-L-Lysine and negatively charged polystyrene sulfonate (PSS).

In various embodiments, the method of producing the film further comprises immobilizing CA via solvent-based covalent attachment on the alkaline-resistant exoskeletal structures of certain biomineralizing algae. Such structure may be strong, naturally-occurring, and/or nanoporous (i.e. inner and outer pores ~750 nm and ~40 nm, algae diameter=30 µm, porosity=37%), alkaline-resistant exoskeletal structures of certain biomineralizing algae. Exemplary structures may include the $CaCO_3$ coccoliths of the marine, photosynthetic coccolithophore algae *Emiliania huxleyi* or the silica frustules of the marine diatom algae *Thalassisora pseudonana*. In various embodiments, meso-porous silica spheres may further be used to pre-immobilize CA prior to incorporation as LbL layer on flat polypropylene membrane. Such pre-immobilization may increase enzyme loading and overall $CO_2$ absorption by the primary MGA.

In various embodiments, use of diatom algae silica as an immobilization support may use a genetically-modified organism, for example, *T. pseudonana*. Such a modified organism may comprise an expression vector encoding enzyme, biosilica-associated sillafin-3 protein, promoter, and/or targeting sequence that may result in targeted localization and stable expression of enzyme at the silica exoskeleton of both (dead or live) parent and daughter cells. In various embodiments, use of diatom algae silica as an immobilization support may reduce and/or eliminate enzyme cost and/or avoid traditionally expensive glucose-based fermentation for enzyme over-expression, lysis/chromatography-based enzyme recovery and purification, and toxic and de-stabilizing solvent-based enzyme immobilization. Diatoms may also uptake additional $Fe_{2+}$ or $Al_{3+}$ ions during photosynthetic growth to make their silica frustule walls more resistant to high pH and high alkalinity of the primary MGA. Moreover, the negative charge of diatom silica may repel inhibitory, accumulating bicarbonate product. Immobilization of CA on such algal structures having diameters of less than about 10 μm and high surface areas with nano-pores similar in size to CA may have additional benefits, including: ensuring that turnover factors approach those of free CA enzyme, promoting high effective $CO_2$ gas-liquid diffusivities, reducing $CO_2$ intra-particular mass transfer resistance, and/or enhancing enzymatic activity, via more degree of freedom to attach to particle's curved surfaces.

In various embodiments, after immobilization of the diatom algae silica, the method may comprise enhancing expression of CA via tethering repetitive catalytic domains to the cell surface to maximize enzyme density.

As used in the bioproduct manufacturing systems described herein, immobilized CA exposure to dry flue-gas components and/or its associated anions ($NO_3$—) and ($SO_4^{2-}$) in solution may not significantly lower CA activity. In various embodiments, to protect the LbL-immobilized CA films in the hollow-fiber primary MGA from hydrodynamic shear and leaching at high gravity or pump-induced liquid solvent flow rates, the interstitial shell-side space of the hollow fiber membrane may be filled with an interpenetrating-network (IPN) cationic pH/ionic-strength sensitive hydrogel. The cationic hydrogel may be aqueous, porous, polymeric, biocompatible, and/or relatively inexpensive. The cationic hydrogel may be responsive to the high pH of the alkaline $CO_2$ solvent recycled from the RACR-PBR algae, such that pores of the primary MGA may open for fast bulk solvent flow and evacuation of inhibitory bicarbonate product through the shell side of the hollow fiber membrane; however, such pores may also be sufficiently rigid to secure and/or enhance structural integrity of the CA film.

In various embodiments, hydrogel porosity at the immediate gas-liquid interface of the hollow-fiber membrane being acidified by the dissolved $CO_2$ may be relatively smaller to help prevent pore-wetting. Finally, catalyst loading may be increased by synthesizing and injecting into the solvent prior to entry into the primary MGA a hybrid gel-artificial enzyme mimic such as, for example, PNipAm-co-CyclenZn. This enzyme mimic may further catalyze $CO_2$ capture at high pH and alkalinity of carbonate-based solvents and/or may precipitate out of bicarbonate-enriched alkaline solution, exiting a primary MGA at a low 33° C. temperature for simple filtration-based recovery and recycling. In various embodiments, the negatively-charged silica immobilization support may repel the inhibitory bicarbonate ion and move it away towards the high convective bulk liquid solvent/enzyme mimic flow on the shell side for rapid evacuation.

Integrated Bioproduct Manufacturing System

Figure 4:
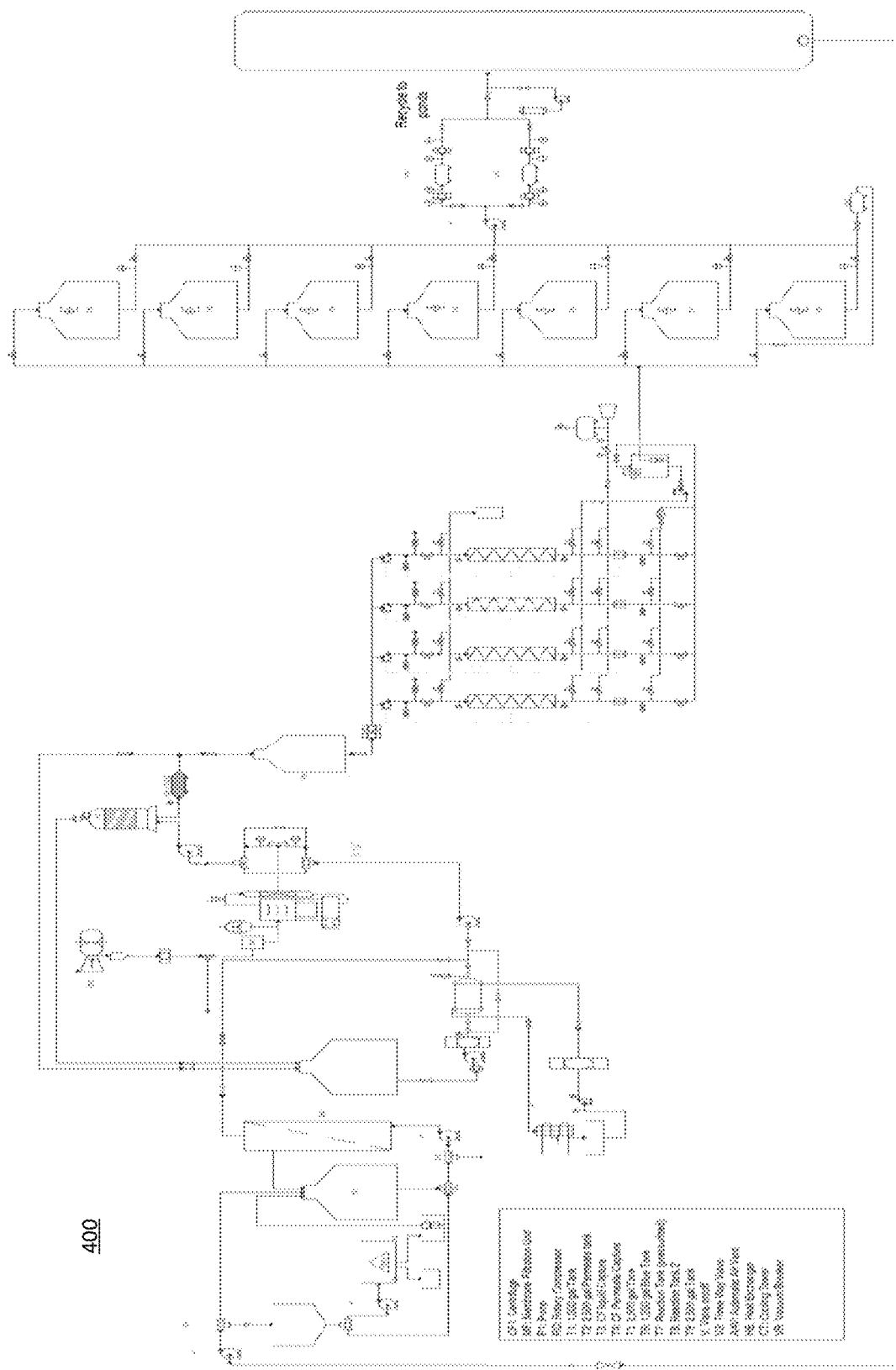
FIG. 4 illustrates a schematic of an advanced oxidation process (AOP) in accordance with an exemplary embodiment.
Figure 6:
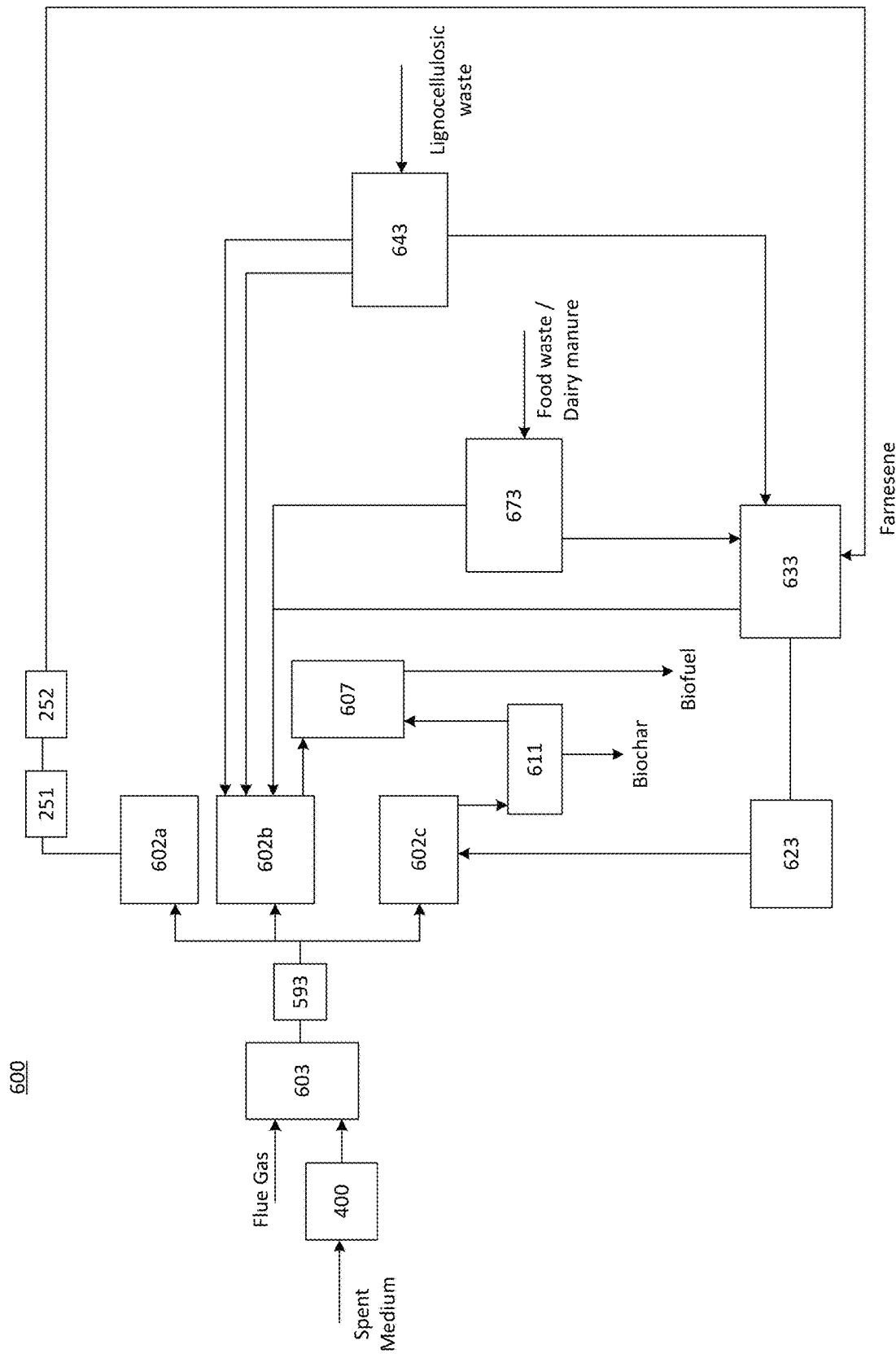
FIG. 6 illustrates a bioproduct manufacturing system in accordance with an exemplary embodiment.

With general reference to FIGS. 1, 4, and 6, in one aspect of the disclosure, integrated bioproduct manufacturing systems and methods are disclosed. There are numerous advantages that stem from the integrated nature of the disclosed bioproduct manufacturing systems. For example, the costs of supplying heat, make-up water, and nutrients to cultivated algae may be reduced and/or minimized by one or more of: (a) supplying C from an absorber that converts $CO_2$ in a gas mixture of oxygen, nitrogen, and carbon dioxide to bicarbonate (b) extracting sensible and latent heat and water from flue gas via a condenser-heat exchanger, (c) oxidizing and dissolving NOx and SOx pollutants in the flue gas via a later-described non-thermal plasma (NTP) and/or soda ash absorber, (d) fractionating wastewater into nitrate, phosphate, ammonia, and/or calcium/magnesium ion fractions that can be used to more controllably supplement other options of the disclosed systems, and (e) supplying organic carbon (e.g., as produced from fractionation of bio-char) for night-time cultivation by cost effectively fractionating lignocellulosic waste biomass.

In various embodiments, levels of calcium and/or magnesium ions in the high pH, high-alkalinity closed-loop cyanobacterial cultivation process may be limited to prevent scaling on the shell-side of a later-described hollow-fibers of a primary MGA and resulting increases in mass transfer resistance or inactivation of a LbL film-enzymatic layer. Levels may be controlled upfront via (1) polystyrene sulfonate ion exchange resin columns to treat incoming fractionated wastewater and/or (2) special Ca2+-selective chelators like EGTA which bind more readily to $Ca_{2+}$ than EDTA. In various embodiments, high-pH stable chelators Fe-HBED and/or Fe-EDDHA may be used supplementally at optimized concentrations to maintain bio-availability of $Fe_{2+}$. Without being bound by theory, such chelators may perform better at high pH conventional chelators.

Figure 5:
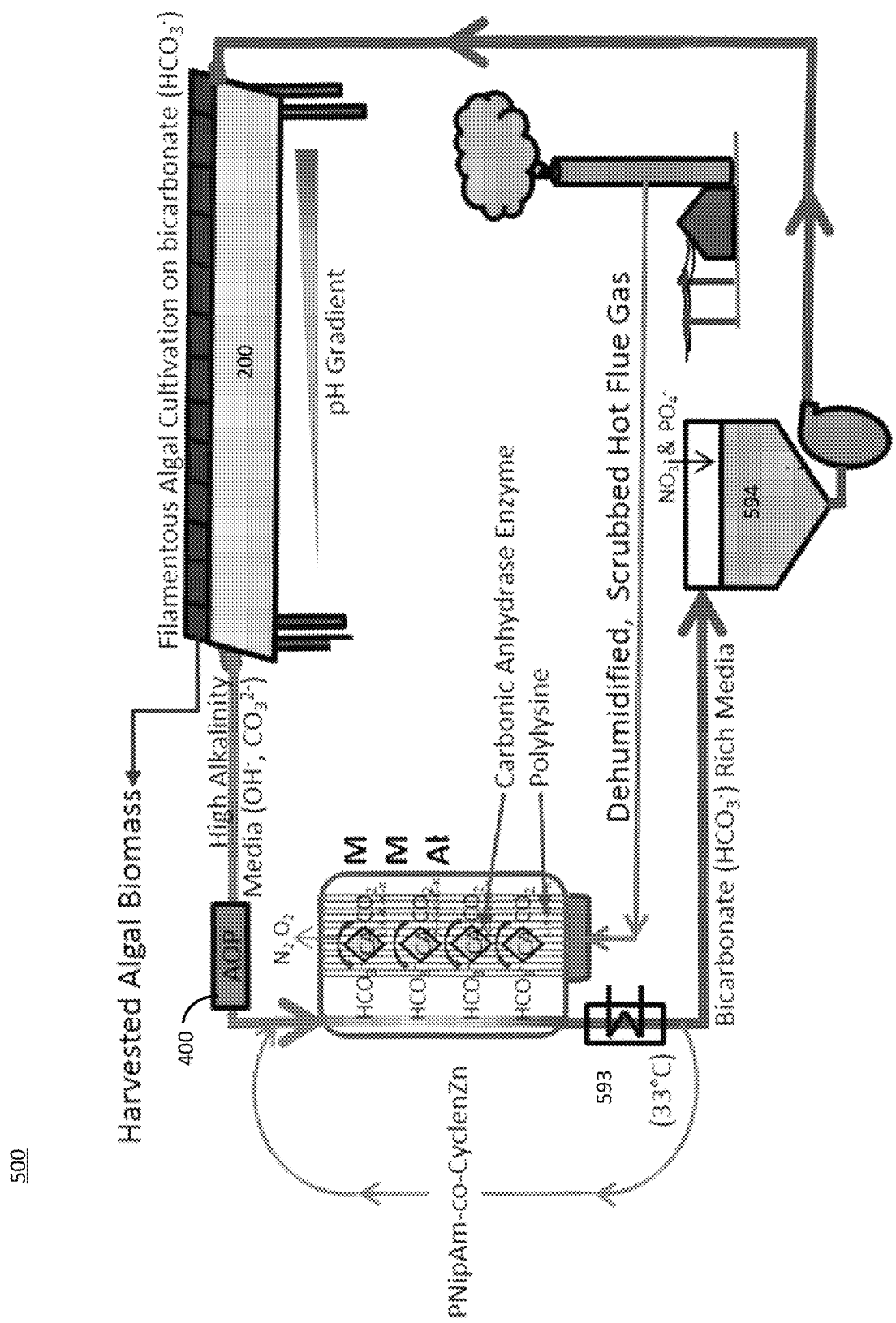
FIG. 5 illustrates a bioproduct manufacturing system in accordance with an exemplary embodiment.

In various embodiments, and with reference to FIG. 5, the levels of organics in the cyanobacterial phototrophic growth medium during the day arising from secretion of polysaccharides, etc. or lysing by death or shear/stress hydrodynamic forces, etc. may be reduced via an advanced oxidation process 400 (AOP). This AOP 400 may include various units of operation and/or inputs. For example, oxidizer/ozone generated via the NTP reactor may be used in AOP 400, to oxidize flue-gas components NOx, SOx, and Hg0 generated in the bioproduct manufacturing system, and/or to pre-treat lignocellulosic biomass, as hereinafter described. This ozone may be generated using cooled, pure photo-evolved $O_2$ collected from RACR-PBR(s) that is combined with the $O_2$ from an integrated pressure-swing adsorber. There may be several benefits to oxidizing in this manner, including: (1) cold temperatures may increase $O_3$ solubility in the alkaline spent algal growth medium, (2) pure $O_2$ may increase the ozone generation yield compared to when using ambient air, (3) removal of $O_2$ in the RACR-PBR headspace may prevent or reduce accumulation that otherwise may inhibit growth via photo-respiratory damage of NPQ/photo-oxidative damage from exposure to high saturation light intensities and dissolved $O_2$ levels.

With momentary reference to FIG. 5, a simplified bioproduct manufacturing system is illustrated. High alkalinity media is removed from a terminal end of a RACR-PBR 200 and subjected to AOP 400. The treated medium is then communicated to a primary MGA where $CO_2$ from the fed gas mixture of oxygen, nitrogen, and carbon dioxide is captured and converted into bicarbonate. The resulting bicarbonate rich medium is then communicated through a condenser-heat exchanger 593 to remove water and extract latent and sensible heat. Prior to reintroducing the enriched medium to an inlet end of RACR-PBR 200, it may be communicated to a buffering tank where N, P, and/or any other necessary constituents beneficial to the RACR-PBR culture may be introduced.

As already described herein, bioproduct manufacturing systems of the present disclosure may comprise one or more RACR-PCRs. Such RACR-PBRs may be configured for cultivation of one or more of filamentous algae, cyanobacteria, microalgae, haloalkaliphilic algae, non-haloalkaliphilic algae, or the like. In one exemplary embodiment and with reference to FIG. 6, a bioproduct manufacturing system 600 may comprise a first RACR-PBR 602a configured for cultivation of a filamentous, haloalkaliphilic cyanobacterium, a second RACR-PBR 602b configured for cultivation of a filamentous, haloalkaliphilic microalgae, and a third RACR-PBR 602c configured for cultivation of a non-haloalkaliphilic microalgae. The RACR-PCRs may be configured for cultivation of freshwater species.

In various embodiments, the RACR-PCR cultures may be fed with a growth medium that is circulated, enriched, and depleted within the integrated bioproduct manufacturing system. For example, growth medium removed from a terminal end of the RACR-PCRs may have been depleted by the RACR-PCR culture. Such depleted growth medium may be treated with an advanced oxidation process 400 (AOP) as described herein. The treated medium may be communicated to a primary MGA 603, as described herein, and enriched with bicarbonate provided at least in part by flue gas, air, or other $CO_2$-containing gas mixture.

In various embodiments, growth of filamentous, haloalkaliphilic cyanobacterium in the first RACR-PBR 602a may result in the production of a gas and/or fluid, which may be communicated to a first condenser 251, from which water way be outlet, and subsequently to a second condenser 252, from which a terpenoid or hydrocarbon may be outlet. In various embodiments, the hydrocarbon comprises farnesene. In various embodiments, the farnesene can be used in part to fire a gas-fired boiler 633, which may provide water to supplement growth mediums in one or more of the RACR-PBRs and/or which may provide a gas mixture of oxygen, nitrogen, and carbon dioxide to a secondary MGA 623.

In various embodiments, growth of non-haloalkaliphilic microalgae in the third RACR-PBR 602c may result in production of wet biomass, which can be treated with a hydrothermal liquefaction process unit 611 to produce bio-char, biogas, bio-oil, and/or an aqueous fraction. In various embodiments, the bio-char is treated and subsequently used as activated carbon for on-site an adsorption processes to de-colorize and/or de-toxify hydrolysate (e.g., remove growth inhibitors including but not limited to furans, furfurals) and acetate solutions from the processing of solid agricultural lignocellulosic waste. The bio-oil may be hydrogenated in a subsequent Co—Fe-catalyzed Fisher-Tropsch synthesis of jet fuel hydrocarbon-alkane blends, or biofuel.

In various embodiments, growth of a filamentous, haloalkaliphilic microalgae in the second RACR-PBR 602b may result in production of hydrogen gas, which may be used, at least in part, for hydrotreatment of bio-oil by a hydrotreatment reactor 607, resulting in the production of biofuel.

In various embodiments, bioproduct manufacturing system 600 may comprise a lignocellulosic biomass pathway configured to use agricultural lignocellulosic waste (for example, wheat straw) in bioproduct manufacturing system 600. For example, such agricultural lignocellulosic waste may be treated with torrefaction 643, resulting in one or more of biogas and bio-oil. In various embodiments, the liquid bio-oil is further refined to produce acetate, which can be used for cyanobacterium cultivation in the first RACR-PLR 602a. Torrefaction 643 of agricultural lignocellulosic waste may also be used for biochemical enzymatic hydrolysis to produce xylose, glucose, and the like, which may then be used for the cultivation of filamentous, haloalkaliphilic microalgae in the second RACR-PBR 602b.

In various embodiments, bioproduct manufacturing system 600 may comprise a waste pathway configured to used food waste and/or dairy manure in bioproduct manufacturing system 600. For example, such material may be digested in an anerobic digester 673. The resulting liquids, referred to herein as wastewater or effluent, may be fractionated and used to supplement growth medium for filamentous, haloalkaliphilic microalgae in the second RACR-PBR 602b. The resulting solids may be used to fire or co-fire gas-fired boiler 633.

The foregoing constitutes a simplified description of various bioproduct manufacturing systems that are within the scope of this disclosure. More detailed description of various components of a biofield production system should be understood to be alternative or complementary to the features described above.

Fractionation of Flue Gas

The bioproduct manufacturing systems described herein may provide improved fractionation of coal-fired flue gas to obtain carbon, nitrogen, water, sulfur, and sensible and latent heat used as inputs for an algal manufacturing and bioproduct manufacturing systems. Fractionation of coal-fired flue gas is achieved with one or more of the following operations: (1) condenser-heat exchanger to remove water for compensating evaporative pond losses and extract both latent and sensible heat to be used in algal processes, (2) dry electrostatic precipitator (ESP) to remove and reclaim fly ash, (3) treatment at the primary MGA to capture and convert $CO_2$ to bicarbonate, (4) non-thermal plasma via dielectric barrier discharge and oxygen from PBRs to convert NO to more soluble $NO_2$, $SO_2$ to $SO_3$, elemental Hg0 to more soluble $Hg_{2+}$, and/or residual $CO_2$ to CO as fuel, and (5) cultivation of cyanobacteria and microalgae in RACR-PBRs.

Both the sensible and latent heat from flue gas can be economically recovered by the bioproduct manufacturing systems disclosure herein, with an upstream condenser-heat exchanger. This heat can be integrated with other processes, included hydrothermal liquefaction of algal biomass, torrefaction of lignocellulosic biomass, anaerobic digestion of food waste or dairy manure. In various embodiments, because the disclosed bioproduct manufacturing systems may use non-thermal plasma, the need for high flue gas temperatures to catalytically oxidize pollutants to make them more soluble for removal is precluded. In such embodiments, sensible heat and latent heat and associated condensed water may be transferred out initially and used instead elsewhere for other applications in the integrated process.

In various embodiments, water is recovered via said condenser-heat exchanger. This water can be used for other processes, including (a) dilution of fractionated wastewater components for accurate formulation, (b) make-up water to compensate for highly evaporative algal or cyanobacterial open-pond or PBR cultivation vessels, (c) as make up water added to the top stage circulating soda ash absorber to compensate for the water evaporated by flue gas from the $Na_2CO_3$ soda ash solution in the absorber, and/or to also maintain the absorber bottom stage solution dissolved solids at a value to maintain the salts in solution (Friedmann 2006). In various embodiments, the NO conversion to $NO_2$ reaction in the NTP reactor may be inversely proportional to the absolute temperature due to the negative activation energy. In various embodiments, $H_2O$ restrains NO oxidation, but $O_2$ enhances oxidation. In such embodiments, NO oxidation to $NO_2$ may benefit from this process's initial heat exchanger-condenser, which both cools the flue gas and dehumidifies it.

In various embodiments, the dry electrostatic precipitator (ESP) is used to remove undesired oxidized mercury ($Hg_{2+}$) and particle bound Hg+ in fly ash. The fly ash, containing silica and alumina, recovered from the dry electrostatic precipitator (ESP) can be discarded, reclaimed, or mixed and used with the highly-effective and selective Purolite A520E ion exchange resin to selectively fractionate out $NO_3$ from other anions ($PO_4^{3-}$) and cations ($NH_{4+}$) in wastewater as a source of N for halo-alkaliphilic cyanobacteria.

In various embodiments, the bioproduct manufacturing system integrates indirect non-thermal plasma (NTP) technologies and dielectric barrier discharge (DBD) reactors with algal cultivation, thereby reducing energy consumption and acid formation because the $SO_2$, $NO_2$ and $Hg_{2+}$ gaseous pollutants that are easily dissolved in water after NTP are directly removed instead by the cultivated microalgae or cyanobacteria, compared to chemical absorption. In those embodiments in which $H_2O$ was previously removed via condenser-heat exchanger, $O_2$ is favorable for $SO_2$, NO, and Hg0 oxidation via indirect NTP-DBD. In various embodiments, residual $O_2$ may exist in the incoming flue gas due to incomplete coal combustion, or it is photo-evolved from phototrophic cultures in one or more RACR-PBRs and/or combined with $O_2$ generated onsite via pressure-swing adsorbers.

In some embodiment, during the NTP process, some NOx will convert to nitric acid or nitrous acid mainly via OH radicals. The algal consumption of nitric acid may be pH neutral as it does not generate H+ (as with ammonia) or OH— (as with nitrate). However, in various embodiments, NO is converted into the more soluble nitrogen dioxide ($NO_2$), which is more easily removed via absorption and algal cultivation. In various embodiments, once NO gas is converted to soluble $NO_2$ gas in this NTP process, it is then rapidly dissolved and separated from the remaining $N_2$ and other trace gases by forming nitrite and nitrate ions and trace CO gas via a soda ash scrubber or absorber using the alkaline spent algal growth medium enriched in $Na_2CO_3$ at high pH 11.5 pumped out of the RACR-PBR.

In various embodiments, $SO_3$ gas is easily oxidized to $SO_2$ gas in the NTP process, and this may be enhanced by both the presence of $H_2O$ and $O_2$. In various embodiments, the recycled alkaline spent algal growth medium enriched in $Na_2CO_3$ at high pH 11.5 pumped out of the RACR-PBR in the soda ash scrubber or absorber to dissolve and react with the $SO_2$ gas from the NTP process. The gaseous and newly oxidized $NO_2$, $SO_2$, and $Hg_{2+}$ from the NTP-DBD are then dissolved and ionized in a novel soda ash absorber that separates these dissolved species from the residual $N_2$ gas and trace amounts of $CO_2$ gas produced using the same spent recycled carbonate/hydroxyl-ion-enriched alkaline growth medium used by the MGA to capture and convert $CO_2$. The resulting $NaNO_2$, $NaNO_3$, and $NaHSO_3$ from this soda ash absorber are then used as cheap N and S nutrients by the cyanobacteria in the RACR-PBR, after $Hg_{2+}$ is first removed in an adsorber via a novel, highly Hg-specific 2-aminothiazole-functionalized polyacrylonitrile resin to selectively remove any dissolved $Hg_{2+}$.

The $Na_2CO_3$ soda ash, alkaline spent growth medium solution will react with $SO_2$ gas in the following Equation 2:

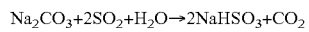

$$Na_2CO_3 + 2SO_2 + H_2O \rightarrow 2NaHSO_3 + CO_2$$

In various embodiments, the spent alkaline medium solvent used in the soda ash absorber to capture the $SO_2$, $NO_2$, and $Hg_{2+}$, may have a high buffering capacity, as it is at pH 11.5. This may allow $NaHSO_3$, in addition to $Na_2SO4$, to be used as a source of S for the RACR-PBR cultures without risking toxicity to the cyanobacteria.

In various embodiments, mercury species may be removed from flue gas with air pollution control devices (APCDs) such as electrostatic precipitator (ESP), fabric filter (FF) and wet flue gas desulfurization (WFGD). In various embodiments, a dry ESP is used. In various embodiments, NTP-DBD is used to oxidize the Hg0 in the flue gas to the more soluble $Hg_{2+}$ or Hg(II). In various embodiments, chemical precipitation, ion exchange, and/or adsorption may be used to remove aqueous $Hg_{2+}$ or Hg(II). In various embodiments, 2-Aminothiazole (AT) monomer, a heterocyclic amine combining the features of pyrrole, thiophene, and aniline, is used for adsorption. In various embodiments, an AT-functionalized polyacrylonitrile resin adsorber is used to separate dissolved $Hg_{2+}$ from the other primary components $NaNO_3$, $NaNO_2$, and $NaHSO_3$, and residual $Na_2CO_3$.

In various embodiments, dissolution of $O_2$ in algal culture may be desirable at night or for indoor cultivation during cold and dark winters in the absence of light when respiration for maintenance or heterotrophic consumption of organic carbon (i.e. glucose, acetate, glycerol, xylose, etc.) may be desirable. In various embodiments, $N_2$ (with trace amounts of $CO_2$) exiting the soda ash absorber, is separated from the $NO_2$, $SO_2$, and $Hg_{2+}$ exiting the NTP-DBD in the soda ash absorber may exist with sufficient partial pressure to serve as a both a source of inert gas to agitate RACR-PBRs for agitation and oxygen removal, and also as a source of N for nitrogen-fixing species cultivated in RACR-PBRs.

Fractionation of Wastewater

In various embodiments, removal of nitrate, phosphate, and ammonia from wastewater of various portions of the bioproduct manufacturing systems described herein may serve as a source of nutrients for the cultures disposed in one or more RACR-PBRs. However, conventional dilution in algal cultures of unfractionated wastewater to provide such N and P-containing nutrients to algal culture may be problematic because it does not account for the uptake and metabolic rates with volatilization rates by the various cultures.

In various embodiments, ammonia from fractionated wastewater can be used for one or more of the following: (1) cultivation as an N-source for various bioproduct manufacturing system operations, (2) as a solvent for $CO_2$-capture and conversion to ammonium carbonate in process of the secondary MGA (later described) which may serve as both N and C source for algae, (3) pre-treatment of lignocellulosic biomass waste, (4) production of fertilizer as ammonium sulfate via an air-stripping process, or (5) in a battery of enzymatic MGA reactors to covert ammonia to nitrate, which for some algae like halo-alkaline tolerant cyanobacteria *Arthrospira platensis* may be the preferred form of nitrogen.

Various methods can be used to fractionate nitrogen (anion $NO_{3-}$ and cation $NH_{4+}$) and phosphate (anion $PO_3{}^{2-}$) from wastewaters at typical wastewater pH values. For example, bioelectrochemical systems may recover nitrogen as $NH_3$ (g) or $(NH_4)_2SO_4$; air stripping of ammonia from anaerobic digestate may be used to recover nitrogen; membrane separation may be used. However, in various embodiments, ion exchange/adsorption-based process may be used herein to provide concentrated streams of reactive nitrogen. In various embodiments, a zeolite ion exchange resin is used to fractionate ammonia from wastewater of the waste pathway disclosed herein. Natural zeolites have a tetrahedral framework where aluminum and silicon atoms are covalently bonded to common oxygen atoms forming interconnected cages and channels.

Regarding nitrate ($NO_{3-}$) removal and its subsequent use as a N source for the haloalkaliphilic cyanobacteria RACR-PBR cultures, several materials such as fly ash, cement, surfactant modified zeolite, alunite, polymeric ion exchangers and agricultural residues may be used in the disclosed systems as adsorbents for the removal of nitrate anions. In various embodiments, a Purolite A520E ion exchange resin is used to fractionate nitrate from wastewater. In various embodiments, ion exchange resins that are more hydrophobic and/or that selectively adsorbs anions having lower hydration energies may be used.

In various embodiments, physical filtration and membrane processes can reduce suspended P for subsequent use as a P source and/or as biocompatible phosphate buffer for the non-haloalkaliphilic microalgae. P can be recovered from wastewater through various other means, including chemical precipitation, acid hydrolysis, coagulation, ion exchange and/or adsorption. In various embodiments, a polymeric ion exchanger impregnated with nanoparticles of hydrated ferric oxide (HFO) sorbent may be used. In various embodiments, the polymer may comprise Lewatit FO36. Lewatit FO36 may be used for removal of $HPO_4^{2-}$, $HSbO_4^{2-}$, and/or SCN— due to its very high selectivity for sorption of oxyanions by the Donnan membrane effect. Lewatit FO36 may have a small affinity for $SO_{42-}$, $NO_{3-}$ and $Cl_-$ ions. Lewatit FO36 may further have regenerability characteristics and high mechanical strength.

In various embodiments, to limit scaling in the disclosed closed loop cultivation scheme containing high levels of bicarbonate and carbonate-based alkalinity, fractionated wastewater may be softened with conventional polystyrene sulfonate-based ion exchange resin adsorption to remove Ca2+ and Mg2+ with NaCl. The MgCl2 and CaCl2 salts removed may later be used to supplement various cultures in a methodical and/or controlled manner, thereby improving efficiency and efficacy of the disclosed bioproduct manufacturing systems.

In various embodiments, wastewater may be fractionated into separate streams of ammonia, nitrate, phosphate, calcium and/or magnesium ions, which may subsequently be used in other operations of the disclosed bioproduct manufacturing systems.

For example, fractionated, concentrated, aqueous ammonia may be used as a cheap, effective solvent for capturing $CO_2$ from torrefaction/biogas-fired flue gas in the secondary MGA. In addition to capturing $CO_2$ with alkaline spent carbonate-enriched growth medium recycled from cyanobacterial RACR-PBR cultures in a primary MGA, the disclosed bioproduct manufacturing systems may also comprise a secondary MGA using ammonia from the wastewater fractionation segment as solvent to capture $CO_2$ from flue gas derived from co-firing relatively cleaner natural gas-fired biogas and/or boiler. In various embodiments, operation of a secondary MGA results in the production of ammonium bicarbonate $NH_4HCO_3$, which is subsequently consumed by one or more cultures disclosed in the RACR-PBRs, for example filamentous microalgae.

In various embodiments, a liquid effluent containing ammonia, Na, K, and phosphate salts is derived from a thermophilic anaerobic digester (AD). The liquid effluent may be subsequently made alkaline via NaOH addition, and/or fed counter-currently to biogas generated from said AD into a stripping process to, for example, strip ammonia, remove $CO_2$ from the biogas, and/or settle out phosphate salts. The gas exiting this stripping process may be subsequently condensed to generate purified biogas ($CH_4$) and/or aqueous ammonium bicarbonate ($NH_3HCO_3$) that can be used as fertilizer, as pre-treatment of ligno-cellulosic biomass as described herein, and/or as N and C-source for algal cultivation.

In various embodiments, the structure of the secondary MGA is similar to that of the primary MGA in that it uses $Na_2CO_3$-containing spent alkaline growth media from RACR-PBR cultures as solvent. In various embodiments, 50 mM of this ammonium bicarbonate serving as both N and C source is supplemented to growth medium and adjusted to starting pH of about 8.0 using a buffer to limit pH increase and/or bicarbonate unavailability, as well as a source of phosphorous for the filamentous, non-haloalkaliphilic microalgae cultivated in a RACR-PBR. In various embodiments, the buffer comprises a 50 mM phosphate buffer; however, any suitable buffer may be used.

The secondary MGA may convert aqueous ammonia to ammonium bicarbonate $NH_4HCO_3$ which may subsequently be used as N and/or C sources by non-haloalkaliphilic microalgae at neutral pH. For example, fractionated, concentrated, aqueous ammonia may be used as a cheap pretreatment of lignocellulosic biomass waste (discussed hereinafter). The pretreatment may comprise 12 hrs. at 42° C.; however, any suitable time and temperature are within the scope of this disclosure. Pre-treatment may be followed by enzymatic hydrolysis. For example, fractionated, concentrated, aqueous ammonia may be used for the production of ammonium sulfate fertilizer via a conventional air-stripping process. For example, fractionated, concentrated, aqueous ammonia may be used for the production of additional nitrate for cyanobacterial cultivation via a battery of 3 enzymatic MGA reactors connected in series and each involving the enzymes to covert ammonia to nitrate, which for some algae like halo-alkaline tolerant cyanobacteria *Arthrospira platensis* is the preferred form of nitrogen.

For example, concentrated nitrate derived from highly-selective ion exchange wastewater fractionation may be used for cyanobacterial cultivation. For example, concentrated phosphate derived from highly-selective ion exchange wastewater fractionation may be used for cyanobacterial cultivation as P source and/or for non-haloalkaliphilic microalgal cultivation as a P source and/or biocompatible buffer. For example, calcium and/or magnesium ions may be added to the cyanobacterial haloalkaliphilic cultures in a deliberate or controlled manner such that the quantities are not excessive and/or that scaling or fouling of MGA membranes is prevented.

Fractionation of Solid Waste

Organic carbon for the first-stage enclosed microalgal cultures can be derived from hydrolysates and/or condensates from processed lignocellulosic agricultural and/or forestry wastes. For instance, a glucose-containing enzymatic hydrolysate from high-temperature ethanol treated rice-straw and/or an acetic acid-containing condensate from fast-pyrolyzed softwood may be used to cultivate the microalgae. Hydrolysates and condensates from treated lignocellulosic biomass may have certain advantages over conventional carbon sources. For example, such hydrolysates contain both $C_6$ and $C_5$ sugars, avoid the "food vs. fuel" controversy, and are more cost-effective and higher-yielding than purchased glucose. For example, such condensates remove carboxylic acids and levoglucosan, stabilize pH, reduce corrosivity, and increase heating-value of an intended bio-oil intermediary product that may later be refined to fuel (i.e. green gasoline) or other chemicals. However, conventional lignocellulosic treatments have significant disadvantages including cost, complexity, and variability.

In various embodiments, the bioproduct manufacturing systems described herein comprise a lignocellulosic pathway configured for utilization of lignocellulosic biomass via thermo-biochemical pre-treatment of lignocellulosic biomass. In various embodiments, the method comprises torrefaction of lignocellulosic biomass. The torrefaction may occur at between about 250-300° C., between about 175-325° C., or at any other suitable temperature. The torrefaction may office in the absence of oxygen and/or in an atmosphere not containing oxygen gas. The lignocellulosic biomass may comprise wheat straw; however, any suitable lignocellulosic biomass is within the scope of this disclosure.

In various embodiments, torrefaction may result in one or more of (1) a dry, brittle, and/or hydrophobic solid biomass, (2) high heating-value gases such as CO and $CH_4$, and (3) a liquid condensate containing a mixture of water and carboxylic acids. Without being bound by theory, these torrefaction-derived acids may arise primarily or completely from the thermochemical degradation of hemicellulose as a by-product, while the pyrolysis-derived acids and phenolic growth inhibitors may arise primarily or completely from the lignin depolymerization as an intended bio-oil product.

The liquid condensate remaining after torrefaction, may require less extensive purification due to the lower temperatures. In various embodiments, the condensate may be used to supply organic carbon (acetate) to a first-stage microalgal culture. In this way, a microalgae that is unable to uptake and/or metabolize directly $C_5$ sugars (i.e. xylose, mannose, ribose) in hydrolysates may instead use the acetic acid in the condensate obtained from the same hemicellulose fraction. The solid biomass remaining after torrefaction may also be further pre-treated with ozonolysis ($O_3$) and soaking in recyclable ammonia, enzymatically hydrolyzed, and purified to supply organic carbon (for example, $C_6$ sugar glucose) to another first-stage microalgal culture.

In various embodiments, lignocellulosic waste biomass is processed in a novel, cost-effective way to ultimately derive acetate, xylose, and glucose for cyanobacterial night-time heterotrophic cultivation. In various embodiments, $O_3$ from the integrated NTP-DBD process and a torrefaction treatment with aqueous ammonia derived from wastewater fractionation is used to pre-treat the biomass. This is far cheaper than the high capital costs and operating costs associated with otherwise pre-treating biomass with high pressure and temperatures in specialized vessels or autoclaves as in the conventional dilute sulfuric acid or steam explosion pre-treatment methods widely adopted.

EXAMPLES

Expression, Purification, and Testing of CA Enzymes

Genes for the halo-alkali-tolerant carbonic anhydrase (CA) from *Aliivibrio salmonicida* and an evolved thermoamine-tolerant CA from *Desulfovibrio vulgaris* were synthesized without a signal sequence and with an N-terminal 6-Histidine tag. Published long-term stability tests show that similar CAs may be suitable biocatalysts for absorption at temperatures below 70° C. Synthesized genes were cloned into pET24(d) and pET24(a) vectors, respectively. Plasmids were transformed into *E. coli* BL21 (DE3), and expression was analyzed after 3 hours expression induced with 0.1 mM Isopropyl β-D-1 thiogalactopyranoside (IPTG). Proteins were expressed at 2 L scale, and *E. coli* cells were disrupted with French press using Bug Buster lysis buffer, freeze-thaw and three rounds of French press (20,000 psi). CAs were then purified using nickel-affinity chromatography by passing clarified cell lysates through a HisTrap™ FastFlow Crude Nickle column (GE Healthcare), washing the column (10 mM Tris pH=8, 250 mM NaCl, 10% glycerol, and 50 mM Imidazole), and eluting (10 mM Tris pH=8, 250 mM NaCl, 10% glycerol, and 500 mM Imidazole) off the column in 1 mL fractions. SDS-PAGE electrophoresis showed presence of CA proteins in elution fractions (Figure).

Based on a BSA Bradford assay, elution fraction E #3 for CA from *A. salmonicida* contained 22.795 mg/ml of protein. Hydration activity of (823.53 U/mg enzyme) for this crude CA based on Wilbur-Anderson units was measured by time required for $CO_2$-saturated seltzer water and enzyme at 4° C. to drop pH of 0.012 M Tris-HCl from pH 8.3 to 6.3. Esterase activity of this CA based on a 4-nitrophenolacetate (NPA) colorimetric assay was measured. A diatom expression vector pfcpSil3-Cy for molecular bombardment-based transformation of the diatom *T. pseudonana* was obtained and sequenced to confirm that it contains genes for mCyanin, sillafin-3, bleomycin, and fucoxanthin promoter.

Lignocellulosic Biomass Processing

Microalgal Strain for Growth Experiments

A multi-trophic (hetero-/mixo-/phototrophic), oleaginous, halo-alkaliphilic green microalgae *Chlorella* sp. ALP2 was isolated and characterized as previously described.

Torrefaction of Wheat-Straw

Wheat straw (*Triticum aestivum*) was obtained in dried farm bails (Grange Supply Co., Pullman, Wash.), ground using a hammer mill, and sieved to 42-60 mesh size with two screens. Approximately 224 g and 570 g were torrefied in a previously described auger reactor at 280° C. and 300° C., respectively, with 7 min residence time and inert $N_2$ gas. This resulted, respectively, in 209.63 g and 383.84 g of solid torrefied biomass collected in a metal cylinder, gas products evacuated by vacuum pump, and 12.1 mls and 147 mls of a liquid condensate (50 mls dark brown primary condensate). To simulate a biorefinery's biomass inventory, all of the non-torrefied and torrefied solid biomass was stored for 14 days in a dry room at 23° C., and the highly-acidic and unstable condensates were immediately frozen at −20° C. for future use.

Analysis of Torrefied and Non-Torrefied Wheat-Straw and Torrefaction Condensate

The torrefied and non-torrefied solid biomasses were comparatively analyzed using SEM imagery, py-GC-MS, FTIR with attenuated reflectance ATR, and TGA, as previously described. The liquid torrefaction condensates were analyzed using GC, pH meter, and Karl-Fisher moisture testing as previously described. The thermal behavior of raw and 300° C.-torrefied wheat-straw under different heating rates was evaluated. Thermogravimetric analysis (TGA) and pyrolysis tests of wheat straw were performed using a TGA analyzer (Mettler Toledo TGA/SDTA 85/e) by heating a typical sample mass of approximately 10 mg placed in 70 μl alumina-ceramic sample holders of a TSO801RO Sample Robot auto-sampler and balance in a purge of nitrogen (50 ml $min_{-1}$), at a preprogrammed linear heating rate of 10, 20, 30, and 40° K $min_{-1}$. The final temperature was 873.5° K, with a holding time of 15 min. For each heating rate, the % converted data was normalized to reflect that heating up to 150° C. was necessary to eliminate the residual water moisture content of the wheat-straw biomass. Conversion was calculated as follows:

$$\alpha = \frac{(m_o - m)}{(m_o - m_\infty)}$$

where $m_o$=100%, $m_\infty$=last corrected TG % value and DTG was calculated as follows:

$$DTG = \frac{(m_{n+1} - m_n)}{dt}$$

For each of the four heating rates the sample temperatures and ln(da/dt) values corresponding to conversions of 0.05 increments in the range of 0.05-0.90 were determined. A first-order reaction rate law with a temperature-dependent rate law constant kA expressed by the following Arrhenius equation was assumed to describe the resulting homogeneous primary thermochemical reactions with negligible mass and heat transfer:

$$k_A(T) = Ae^{-\frac{E_a}{RT}}$$

where A=Pre-exponential factor or frequency factor, $E_a$=Activation Energy (J/mol), T=Absolute temperature (° K), and R=Gas constant=8.314 J/mol ° K. Milling of the wheat-straw to 42-60-mesh size and use of an inert nitrogen carrier gas ensured rapid heat and mass transfer and avoidance of undesirable secondary thermochemical reactions. The isoconvensional Friedman method, which assumes that the reaction rate (da/dt) at a constant conversion is only a function of temperature, was applied to thermogravimetric data. This was used to determine kinetic parameters for a first-order reaction rate law assumed to describe homogeneous primary thermochemical reactions with negligible mass and heat transfer. A plot of ln(da/dt) vs. 1000/T(° K) for each conversion was generated. The activation energies were calculated from the slopes of each relatively straight line as follows:

$$\text{slope} = \frac{-E_a}{R}$$

The Arrhenius pre-exponential factors were calculated from the x-intercepts of these relatively straight lines as follows where a reaction order n of 1 was assumed:

ln A=x–intercept–n ln(1–α)

The ASTM E1641-04 integral method was alternatively used. The vaporized products from primary reactions of fast pyrolysis of 280° C.-torrefied and non-torrefied wheat straw were also comparatively obtained and analyzed on a py-GC-MS instrument (Agilent) with a calibrated oven temperature of 500° C. and heating rate of 800° C./min as previously described. For this, samples of 1.54 mg and 0.620 mg were weighed for 280° C. and 300° C.-torrefied and raw wheat-straw, respectively using the aforementioned TGA instrument.

Preparation and Analysis of Wheat Straw Hydrolysate

To generate hydrolysate, 10 g of 280° C.-torrefied and non-torrefied biomass were soaked at 10% (w/v) overnight in de-ionized water and ozone-lyzed in a metallic batch reactor as previously described in 2.5 g-increments for 30 min with air/$O_3$ flow-rate of 5 L/min. Approximately 7.63 g of biomass was then used for subsequent pre-treatment. This involved soaking at 10% (w/v) in an aqueous 28-30% (w/v) $NH_4OH$ solution (JTB-9721-03) and incubating at 50° C. for 12 hours with no agitation in 1-L screw-cap Pyrex solution bottles. The biomass was then washed thoroughly with 0.8 L de-ionized water through a vacuum-pressurized Whatman filter until neutral pH 7.0 in the permeate was reached. The resulting filter-cake (g) was dried at 50° C. for 8 hrs. Then 4 g of this was enzymatically hydrolyzed at 50° C. in capped flask in an orbital incubator shaker (Gyromax 747) for 72 hrs. This occurred at 4% (w/v) solid loading in 0.050 M sodium acetate buffer (pH 4.8) supplemented with 8 mls of solution containing 2% sodium azide with 30 FPU/g of cellulase (Novozymes NS 50013) and 30 CBU/g of β-glycosidase (Novozymes NS 50010). Enzymatic hydrolysis was terminated by boiling the hydrolysate in a hot water bath for 5 min and centrifuging for 10 min at 3000 rpm (x g) to remove residual insoluble lignin particulates. About 48 mls of light-brown hydrolysate was then decolorized and detoxified by adding 2.4 g Darco 20-40 mesh activated charcoal (Sigma Aldrich, St. Louis, Mich.) at a 5% (w/v) loading, briefly vortexing, and incubating for 12 hours at 4° C. The activated charcoal used for de-toxifying non-torrefied hydrolysate was also vigorously vortexed and incubated for 16 hours at 4° C. in acetone and methanol solvent in 1 ml Eppendorf tubes and then PTFE 0.2 um disc-filtered away to remove coloration compounds for their analysis on GC-MS as previously described. The resulting black slurry was centrifuged, and grey supernatant was vacuum-filtered with Whatman paper. The clear permeate was then neutralized to pH 7 via addition of 1M NaOH, sterilized with 0.2 μm disc-filter for subsequent mixotrophic microalgal cultivation, and analyzed for sugar content.

Additional non-detoxified hydrolysates of both non-torrefied and torrefied biomasses derived instead by 2% solid loading and using instead the 0.050M sodium citrate buffer specified in an NREL standardized method were also comparatively analyzed for sugar content and ability to be used for microalgal cultivation. The final acetate-buffering and de-toxification steps to generate the hydrolysate used for microalgal cultivation were devised after preliminarily observing that citrate buffer did not permit growth consistent with literature and that 33% and 50% dilutions of the brown hydrolysate with de-ionized water allow progressively greater microalgal growth.

Preparation and Analysis of Purified Wheat Straw Torrefaction Condensate

Of the 50 mls of thawed condensate (bio-oil), 4 mls was set aside for Karl-Fisher moisture testing. In two separate tubes, about 23 mls condensate was diluted with 11 mls cold de-ionized water and agitated horizontally in 50 ml plastic tubes on orbital flask for 1 hour to precipitate out phenolic-containing resins that adhered to tube walls. Each supernatant was then neutralized with 6 mls of 10N KOH base addition from pH 2.54 to 7.00 to prevent volatilization of acids and then centrifuged at 4000 rpm (x g) for 10 min to separate away any residual solids. The supernatants were extracted 1:1 (v/v) with ethyl acetate as the top layer. These were than distilled at vacuum pressure (~30 torr) at 60° C. for 20 min with 30 rpm rotation with cooling water and a three-bulb collector distillation unit (Rota-Vap). A total of 70 mls was collected in the bottom bulb. The clear liquid that boiled away and condensed in the middle second bulb collector was later analyzed for $_1$H-NMR analysis. About 45 mls of the condensate remaining in the bottom-bulb was then incubated overnight at 4° C. at 5% (w/v) with a combination of 3.26 g regular and 3.26 g $O_3$-treated activated-carbon. $O_3$-treatment was carried out as previously described to add repulsive negatively charged surface-moieties which prevent adsorption losses of valuable acetate ions. The liquid condensate was then filtered with Whatman-paper under vacuum and then 0.45 μm and 0.2 μm disc filters, yielding a 34 mls of a yellow and clarified condensate. A 100× dilution of this supported algal growth but with long lag-phase. Therefore, 25 mls of the condensate underwent the vacuum distillation procedure again but this time for an additional 1.5 hours. About 3.5 mls of dark-orange, viscous distillate containing non-volatilized carboxylate salts that were retained in the first bulb collector was allowed to cool and re-suspended back to 25 mls with de-ionized water to enable collection and filtration. About 9.5 mls and 4 mls of clear liquid were also collected in the large top bulb and center mid-bulb, respectively. Carboxylic acid and ethanol content of the final purified and de-toxified condensate was measured by withdrawing a small sample, lowering its pH to 2.5 with HCl acid, and loaded onto a GC as previously described.

Preparation of Effluent and Biogas from Anaerobic Digestion of Food, Manure, and Torrefaction Condensate Food waste effluent was obtained from the 7-day processing of American-style food waste from a Washington State University (WSU) cafeteria in a system comprised of a high-solids anaerobic digester with recycling seed (SADRS) for hydrolysis and an Up-Flow Anaerobic Sludge Blanket (UASB) reactor for methanogenesis described elsewhere.

Approximately 20 L/day of biogas on average comprising 62% CH4, 37% $CO_2$, at 0.29 L $CH_4$/g volatile solids food waste and 19.2 L/day of food waste effluent was generated. Flush dairy-manure waste effluent was derived from Sequential Batch Reactor (SBR) as previously reported. To initially test if effluent alkalinity and salinity sufficiently prevented ammonia volatilization losses at high temperatures and to sterilize preliminary comparative flask cultures, both effluents were autoclaved for 25 min at 121° C. and 101.1 kPa gauge pressure and subsequently analyzed with an alkalinity meter and Kjeldahl digestion method. Samples from cultures involving manure effluent were also analyzed on a flow cytometer (BD FACSCalibur) for scattering and fluorescence as previously described. For subsequent microalgal growth experiments, both effluents were instead briefly vortexed to remove adsorbed N and P species from suspended particles and sterilized under vacuum with 0.2 µm filtration (Millipore) to remove contaminating bacteria and, in the case of manure effluent, suspended particles that obfuscate microalgal dry cell weight and UV-Vis spectrophotometric measurements.

Biomass, Lipid, and Extracellular Concentration Measurements

Dry cell weight (DCW), chlorophyll a/b and carotenoid content, extracellular pH, light intensity, optical density (OD) were measured as previously described. Absorbance maxima at $OD_{680}$ corresponding to algal chlorophyll was not found to be correlated to absorbance minima at $OD_{750}$. Separate standard curves were generated for heterotrophic and phototrophic cultures because $OD_{680}$ depends on dynamic microalgal optical properties (i.e. Mie-scattering and Beer's Law absorption extinction cross-sections, which are related to chlorophyll LHCII antenna size and cellular dimensions) that, in turn, are dependent on the incident light intensity. A standard curve correlating heterotrophic $OD_{680}$ and DCW for ALP2 was therefore developed with linear regression as follows:

DCW(g/L)=$OD_{680}$×0.4007−0.0172, $R^2$=0.9734

Similarly, a standard curve correlating phototrophic $OD_{680}$ and DCW for ALP2 was developed:

DCW(g/L)=$OD_{680}$×0.3713+0.1617, $R^2$=0.9068

Specific growth rates during the exponential growth phase between initial ($t_1$) and final ($t_2$) time points were calculated as previously described. Total carbon and inorganic carbon in supernatant were measured using a TOC-5000 analyzer (Shimadzu, Kyoto, Japan). Total nitrogen was measured using a spectrometer and total high-range (10-150 mg/L) colorimetric reagent Test N Tube kits (Hach Company, Loveland, Colo.). An un-inoculated flask containing BG-110 medium, adjusted to pH 9 and supplemented with 2.5% (v/v) effluent and 17.0 g/L $NaHCO_3$, was agitated to determine its ammonia volatilization rate, based on periodic measurement of total nitrogen in the medium. Neutral lipid content was assessed for the majority of ALP2 cultures via $_1$H NMR, as previously described. Lipid content and fatty-acid profiles for ALP2 cultures grown heterotrophically at 28° C. and 21° C. at 10 g/L and 20 g/L glucose, or phototrophically on food waste effluent, were assessed by a previously described FAME GC-based procedure.

Evaluation of Second Stage Cultivation Conditions

ALP2 was centrifuged, washed 1× in PBS, and inoculated at an $OD_{680}$=0.035 from 14-day maintenance cultures into 250 ml flasks containing 100 mls of BG-$11_0$ media devoid of $KH_2PO_4$ and supplemented with different anaerobically-digested food waste effluent concentrations (5%, 10%, 15%, 22% (v/v)) and different $NaHCO_3$ concentrations (8.4 g/L, 16.8 g/L, 25.2 g/L, 33.6 g/L) with pH either un-adjusted or daily adjusted to 9.0 via HCl acid. The flasks were agitated at 150 rpm on orbital shaker under 75 µmole $m_{-2S-1}$ PAR light intensity delivered by polychromatic fluorescent light bulbs overhead. These cultures were monitored for $OD_{680}$, pH, flow cytometric BODIPY-488 stain-based lipid content (1.5 ml day 10), chlorophyll-fluorescence (1.5 ml day 4), $O_2$-evolution, and respiration. Finally, 50 ml and 20 ml samples were withdrawn for measuring biomass dry cell weight and FAME-GC-derived lipid content, respectively.

Demonstration of Two-Stage Cultivation

A two-stage cultivation process was demonstrated using the organic carbon, nitrogen, and phosphorous from biological waste. For two simultaneous first-stage mixotrophic cultures, ALP2 from maintenance culture was centrifuged, washed 2× in PBS, and inoculated at an $OD_{680}$=0.50 into two foam-capped 50 ml flasks. These two flask cultures were agitated at 150 rpm on orbital shakers under 75 µmole $m_{-2S-1}$ light intensity from overhead polychromatic fluorescent bulbs and contained $^{25}/_{30}$ mls of 0.2 µm-filtered BG-$11_0$ adjusted to pH=7.0 with 1M NaOH, supplemented with 1.587 g/L urea and either (1) torrefied wheat-straw hydrolysate diluted to 10 g/L glucose or (2) torrefied-wheat-straw condensate diluted to 0.35 g/L potassium acetate. Such dilutions of condensate and hydrolysate further ensured lower concentration of inhibitory compounds (i.e., phenolics, furans (HMF and aldehydes)) for microalgal cultivation. (It contained 25 mls of modified BG-11 medium supplemented with 0.250 mls of purified condensate representing a dilution to approximately 0.35 g/L potassium acetate). These were cultivated mixotrophically to near-stationary phase. The cells from these two cultures were then washed 1× with PBS to remove any residual nitrogen, organic carbon, and phosphate. They were then inoculated at $OD_{680}$=0.250 each for a combined total of $OD_{680}$=0.500 corresponding to a cell density of 2.5×$10_6$ cells/ml into a second-stage, foam-capped 250 mls Erlenmeyer flask. This second-stage flask culture was cultivated phototrophically at 22° C. under 75 µmoles $m_{-2S-1}$ photon flux density from overhead polychromatic fluorescent light bulb, agitated at 150 rpm on orbital shaker, and contained 100 mls of BG-110 medium devoid of $KH_2PO_4$ and supplemented with 16.8 g/L $NaHCO_3$ and 2.5% (v/v) of 0.2 µm-filtered anaerobically-digested food waste effluent, at a pH 10 that was daily adjusted initially with 0.5M HCl acetic acid.

Intracellular and Extracellular Cultivation Measurements

Optical density (OD) at 680 nm, dry cell weight from 0.5M $NH_3HCO_3$-washed culture samples, haemocytometric cell density, chlorophyll a/b content, specific growth rate, alkalinity, pH of culture media and lake water, light intensity, total carbon and inorganic carbon, total nitrogen and ammonia nitrogen, and were measured and calculated as previously described. Total phosphate $PO_4^{3-}$ and Chemical Oxygen Demand (COD) were measured as reported. Alkalinity of effluent and culture supernatants was measured using Mettler Toledo T-50 Rondolino analyzer as reported as mg/L of $CaCO_3$. Total $NH_{4-}$ N composition of effluent and culture supernatants was measured using a Tecator 2300 KJELTEC analyzer. A standard curve correlating phototrophic $OD_{680}$ and DCW was developed with linear regression as follows:

$$OD_{680} = DCW(g/L) \times 0.4007 - 0.0172, R^2 = 0.9734$$

Absolute intracellular neutral lipid content was assessed using liquid-state $_1$H NMR and a FAME GC-FID procedure, as previously described. Relative intracellular neutral lipid content and the relative densities of chlorophyll-fluorescent microalgal ALP2 cell populations and non-fluorescing anaerobic digestion effluent debris were obtained using a benchtop FACSCalibur flow cytometer equipped with CellQuest software (BD Biosciences, San Jose, Calif.) as previously described. BODIPY 488-staining of 1×PBS-washed culture samples was performed using a previously described procedure whereby 0.5 mls of ALP2 microalgal culture was stained directly with 1 μM BODIPY-488 in TFE solvent and incubated for 5 min. These and non-stained auto-fluorescent negative control samples were then flow cytometrically acquired. The ratio of FL1 of stained to that of the unstained sample gave the normalized fluorescences, and this was used to compare the ALP2 relative neutral lipid content at different conditions. Extracellular content of $C_5$ (i.e. xylose, mannose, ribose) and $C_6$ (glucose, galactose) monomer sugars from first-stage mixotrophic cultures and in hydrolysates before and after de-toxification was analyzed with a Dionex Ion-Exchange-HPLC (Agilent) equipped with amperimmometric/FID detector as previously described.

Recombinant Enzyme Expression and Purification

The gene encoding the halo-alkali-stable carbonic anhydrase (ACA) from *Aliivibrio salmonicida* LFI1238 (Codexis) was synthesized with an N-terminal 6-Histidine tag, and cloned in pET24d plasmid vector with NcoI and BamHI restriction enzyme. That encoding an evolved thermo-amine-stable carbonic anhydrase (CCA) from *Desulfovibrio vulgars* was synthesized with no signal sequence, an N-terminal 6-Histidine tag, and cloned in pET24a with NdeI and BamHI. Published long-term stability tests show that CAs similar to ours were suitable for $CO_2$ absorption at temperatures below 70° C. BL21 (DE3) cells were transformed with these plasmid vectors, Purified colonies were grown overnight and diluted 1:50 in 2 L of LB with Kanamycin (25 ug/mL) and grown 2 hours. Isopropyl β-D-1 thiogalactopyranoside (IPTG) was added at a final concentration of 0.1 mM for induction, and cells were grown an additional 3 hours, spun, and frozen at −80. Cells were resuspended in 25 mL French Press lysis buffer (50 mM Tris pH 8, 100 mM NaCl, 0.1 mM EDTA, 0.1% Tritons X-100, and 5 ug/mL lysozyme) and freeze-thawed 2 more times before 2.5 mL of Bug Buster lysis buffer, 0.1 mM PMSF, and 25 uL of HALT protease inhibitor were added and all was passed through the French press at 20,000 psi for 4 passes. Low- and high-speed spins were 4000 and 20,000 rpm, respectively. CAs were then purified using immobilized metal nickel-affinity chromatography (IMAC) by passing clarified cell lysates through an equilibrated HisTrap™ FastFlow Crude Nickle column (GE Healthcare), washing the column, and eluting off the column in 1 mL and 5 mL fractions for CA from pET24d-6HisCA and pET24a-6HisCA, respectively. Equilibration Buffer consisted of 10 mM Tris pH=8, 125 mM NaCl, 10% glycerol, and 10 mM Imidazole. Wash Buffer consisted of: 10 mM Tris pH=8, 250 mM NaCl, 10% glycerol, and 50 mM Imidazole. Elution Buffer consisted of 10 mM Tris pH=8, 250 mM NaCl, 10% glycerol, and 500 mM Imidazole. SDS-PAGE electrophoresis was performed to assess proper size, yield, and purity.

Membrane Gas Absorber Configuration and Operation

Bovine carbonic anhydrase (BCA) (Sigma Aldrich, St. Louis) was purchased as standard enzyme. For free enzyme characterization, BCA was weighed and dissolved in 0.050 M Tris-HCl, pH 8.0 at 1 mg/mL. The protein concentration of the recombinant, purified CCA and ACA were quantified via Bradford assay with bovine serum albumin (BSA) standard (Bio-Rad). CCA and ACA were diluted in in 0.050 M Tris-HCl, pH 8.0 at 1 mg/mL. All three enzymes were assayed for esterase activity with 4-NPA substrate and for $CO_2$-to-bicarboante conversion hydration activity with dissolved $CO_2$ substrate. For free esterase activity, 3 mM 4-NPA was prepared by dissolving 13.6 mg in 1 ml acetone and then voluming up to 25 mls in DI water. Aliquots of 0.2 ml enzyme solutions were incubated for 4 hours at either T=25 C, 37 C, 50 C, and 62 C in 0.050 M Tris-HCl, pH 8.0 buffer, or T=25 C in 0.050M Tris-HCl at pH=6, 7, 8, 9, and 10 and then assayed for esterase activity in microplates with UV-Vis spectrophotometer at 348 and 400 nm in 200 uL reactions consisting of volume proportions of 1.8 ml 0.050 M Tris-HCl pH 8.0 buffer+1.0 mls of 3 mM 4-NPA and 0.2 ml of 1 mg/ml enzyme solution. Michaelis-Menten enzyme kinetic parameters were determined by assaying at 0, 0.5, 1, 2, 3, and 4 mM 4-NPA substrate concentrations. For free hydration activity, the Wilbur-Anderson assay was performed where enzyme was either diluted in 0.050 M Tris-HCl, pH 8.0 to either 0.1 or 0.01 mg/ml, chilled on ice, and then dispensed in a small, magnetically stirred 100 mL beaker containing 6 mls of 0.012 M Tris-HCl, pH 8.0 to which 4 mls of saturated 70 mM $CO_2$ seltzer water was added and time for pH decrease from 8.3 to 6.3 at 4 C was recorded. Michaelis-Menten enzyme kinetic parameters were also determined at $CO_2$ substrate concentrations of 0, 8.75, 17.5, 35, 52.5, and 70 mM $CO_2$. ACA enzyme dilutions were also prepared with final 100 pM-10 mM $ZnCl_2$ to ensure zinc availability for the metalloenzyme hydration activity.

The BCA, CCA, ACA enzyme dilutions were immobilized and tested via adsorption and covalent bonds on beads as follows: Amberlite XAD7HP beads with acrylic surface groups (Sigma, St. Louis) were weighed at 0.125 mg for a 5:1 (material g/enzyme g) ratio, washed in PBS, pH 7.4 and distilled water three times, and vacuum filtered. BCA which was weighed at 25 mg and ACA were both diluted to 3 mg/ml in 0.050 M Tris-HCl, pH 8.0 for a total of 25 mg enzyme in 8.3 ml solution for each immobilization reaction. CCA was diluted only to 1 mg/ml, given the low quantity available. BCA, CCA, and ACA enzyme was incubated for 2 hours in parafilmed 250 ml shaker flasks at 150 rpm at 30 C, and BCA was alternatively incubated also at 37 C. A 25% (v/v) solution of glutaraldehyde was added to the 4 incubation reactions to a final 2.5% (v/v) concentration to crosslink enzyme via covalent bonds. The mixtures were then washed repeatedly in PBS and vacuum-filtered. Samples of the permeate were saved to later analyze the efficiency of immobilization. The resulting retentate beads were dispensed in glass vials, dried under vacuum in a lyophilizer at room temperature, and later used for aforementioned assays for esterase and hydrolase activity. To test adsorption-only immobilization, 1 g of beads+50 mls of a pooled ACA elutions, 0.125 mg beads+8 mls of pooled CCA elutions, and 0.125 mg beads+8 mls of pooled BCA residual solutions were similarly incubated but not cross-linked and assayed. Esterase activity was measured for 3 beads of crosslinked, immobilized BCA, CCA, and ACA.

Unlike the other enzyme immobilization incubation mixtures that turned yellow after cross-linking with glutaraldehyde, ACA apparently denatured. Free ACA had the highest $CO_2$-to-bicarbonate hydration activity of 823.53 U/mg enzyme. Kinetic term $Km/V_{max}$ for free BCA was 0.010. Crosslink-immobilized BCA at 30 C incubation had the highest hydration activity of 5.74 U/mg beads and was higher than the same BCA at 37 C incubation. It is noted that CCA beads were cross-linked immobilized with significantly lower quantities of enzyme that also likely lost activity after storage as liquid solution at 4 C for 2 months. Some hydration activity was detected in adsorbed-immobilized ACA, but weak adsorption forces probably were insufficient at retaining most of this and this and the other enzymes on beads.

Esterase activity was highest for free BCA at pH 8 and 50 C, and lowest for free ACA. Still, the expectedly thermo-alkaline-stable free CCA exhibited high esterase activity at high temperatures and pH. The Km=77.75 mM 4-NPA and $V_{max}$=416.67 U/mg enzyme for free CCA. The Km=311.714 mM 4-NPA and $V_{max}$=714.286 for free ACA. For cross-linked enzyme, esterase activity was highest for the CCA having less enzyme, where a slight change in absorbance of 0.288-0.230 was actually measured.

Membrane Gas Absorber Configuration and Operation

Two small-scale 0.5×1 flat-sheet polypropylene G591 micromodule membrane gas absorbers (MGA) and one cylindrical 2.5×8 hollow-fiber polypropylene G470 MGA were purchased (3M, Charlotte, N.C.). A G591 MGA was configured with Tygon tubing, flowmeter, and pressure regulator to deliver pure $CO_2$ from a compressed gas cylinder at 1 psi at 25 L/min. The G591 was also connected to a peristaltic pump to deliver at 100 ml/min either 200 mM $NaHCO_3$, pH 10 or 0.2 μm-filtered, spent BG-11 growth medium with 200 mM $NaHCO_3$, pH 9.79 that was collected from one of our Anabaena strain 500-2A growing phototrophically long-term in 1L Roux bottles. The crosslinked and non-crosslinked bead-immobilized BCA, ACA, and CCA enzymes, as well as negative control beads containing no enzyme, were for each test injected by syringe at the downstream liquid-side end of the MGA just beyond the flat-sheet membrane and before a 60 μM stainless-steel filter housing. Rate of pH decrease of alkaline solution exiting the MGA into a beaker with and without $CO_2$ gas flow was measured for each type of bead.

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection. When language similar to "at least one of A, B, or C" or "at least one of A, B, and C" is used in the specification or claims the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. A bioproduct manufacturing system, comprising:
    a hollow-fiber primary membrane gas absorber comprising a shell side and a lumen, wherein the primary membrane gas absorber is configured to receive a carbonate salt-based solvent on the shell side and a gas mixture comprising oxygen, nitrogen, and carbon dioxide in the lumen;
    at least one runway algal cassette reactor-photobioreactor comprising:
        at least one growth chamber coupled to and in fluid communication with a headspace channel so as to define an interior volume;
        a first condenser coupled to and in fluid communication with the headspace channel; and
        a harvest line in fluid communication with the at least one growth chamber and coupled to a filter;
    a growth medium circulating between the primary membrane gas absorber and the at least one runway algal cassette reactor-photobioreactor, wherein the primary membrane gas absorber is configured to receive the growth medium from the at least one runway algal cassette reactor-photobioreactor in a bicarbonate-depleted state, and the at least one runway algal cassette reactor-photobioreactor is configured to receive the growth medium in a bicarbonate-enriched state;
    carbonic anhydrase enzyme immobilized on a hollow fiber surface of the primary membrane gas absorber; and
    an immobilization support on the hollow fiber surface of the primary membrane gas absorber, the immobilization support comprising diatom algae silica.

2. The bioproduct manufacturing system of claim 1, further comprising linear primary amine poly-L-Lysine immobilized on a hollow fiber surface of the primary membrane gas absorber.

3. The bioproduct manufacturing system of claim 2, wherein a soluble enzyme mimic PNipAm-co-CyclenZn is communicated to the growth medium when it is in a bicarbonate-depleted state.

4. The bioproduct manufacturing system of claim 1, further comprising a secondary condenser coupled to the headspace channel and configured to condense a volatile terpenoid secreted by organisms disposed in growth chambers.

5. The bioproduct manufacturing system of claim 1, further comprising at least one cassette disposed in the at least one growth chamber.

6. The bioproduct manufacturing system of claim 1, further comprising a vacuum pump in fluid communication with the headspace channel and downstream of the first condenser.

7. The bioproduct manufacturing system of claim 1, wherein the at least one runway algal cassette reactor-photobioreactor comprises an elongated shape and is configured to establish a spatial gradient of pH and alkalinity that increases towards a terminal end of the at least one runway algal cassette reactor-photobioreactor.

8. The bioproduct manufacturing system of claim 1, further comprising at least one of a non-thermal plasma reactor, a dielectric barrier discharge reactor, and a soda ash absorber.

9. The bioproduct manufacturing system of claim 1, further comprising at least one of a hydrothermal liquefaction process unit and a hydrotreatment reactor.

10. The bioproduct manufacturing system of claim 1 wherein the at least one runway algal cassette reactor-photobioreactor comprises a first RACR-PBR configured to cultivate a filamentous, haloalkaliphilic cyanobacterium, a second RACR-PBR configured to cultivate a filamentous, haloalkaliphilic microalgae, and a third RACR-PBR configured to cultivate a non-haloalkaliphilic microalgae.

11. The bioproduct manufacturing system of claim 1, further comprising a secondary membrane gas absorber.

12. The bioproduct manufacturing system of claim 1, wherein the diatom algae silica comprises a modified organism comprising at least one of an expression vector encoding enzyme, basilica-associated silliafin-3 protein, promoter, and targeting sequence.

13. A bioproduct manufacturing system, comprising:
a hollow-fiber primary membrane gas absorber comprising a shell side and a lumen, wherein the primary membrane gas absorber is configured to receive a carbonate salt-based solvent on the shell side and a gas mixture comprising oxygen, nitrogen, and carbon dioxide in the lumen;
at least one runway algal cassette reactor-photobioreactor comprising:
at least one growth chamber coupled to and in fluid communication with a headspace channel so as to define and interior volume;
a first condenser coupled to and in fluid communication with the headspace channel; and
a harvest line in fluid communication with the at least one growth chamber and coupled to a filter;
a growth medium circulating between the primary membrane gas absorber and the at least one runway algal cassette reactor-photobioreactor, wherein the primary membrane gas absorber is configured to facilitate conversion of carbon dioxide gas disposed in the gas mixture into soluble bicarbonate disposed in the growth medium;
carbonic anhydrase enzyme immobilized on a hollow fiber surface of the primary membrane gas absorber; and
an immobilization support on the hollow fiber surface of the primary membrane gas absorber, the immobilization support comprising diatom algae silica.

14. The bioproduct manufacturing system of claim 13, further comprising:
a lignocellulosic biomass pathway configured to pre-treat lignocellulosic biomass with torrefaction to produce at least one of biogas, bio-oil, and bio-char, wherein the bio-oil is refined to produce acetate, and wherein the acetate and the bio-char are communicated to the at least one runway algal cassette reactor-photobioreactor, wherein the lignocellulosic biomass comprises wheat straw.

15. The bioproduct manufacturing system of claim 13, further comprising: a waste pathway comprising at least one ion exchange resin, wherein the waste pathway is configured to fractionate wastewater from an anaerobic digestion of at least one of food waste and manure to recover nitrogen and phosphorous.

16. The bioproduct manufacturing system of claim 15, wherein the at least on ion exchange resin comprises at least one of a zeolite ion exchange resin, a Purolite ion exchange resin, and a polymeric ion exchanger impregnated with nanoparticles of hydrated ferric oxide.

17. The bioproduct manufacturing system of claim 15, wherein the waste pathway further comprises a polystyrene sulfonate-based ion exchange resin.

18. The bioproduct manufacturing system of claim 13, further comprising:
a non-thermal plasma reactor configured to oxidize NOx and SOx pollutants in the gas mixture to produce NO2 and SO3 gas; and
a soda ash absorber configured to receive NO2 and SO3 gas and to produce NaHSO3+CO2, wherein the NaHSO3+CO2 is used to enrich the growth medium.

19. A bioproduct manufacturing system, comprising:
a hollow-fiber primary membrane gas absorber comprising a shell side and a lumen, wherein the primary membrane gas absorber is configured to receive a carbonate salt-based solvent on the shell side and a gas mixture comprising oxygen, nitrogen, and carbon dioxide in the lumen, and wherein carbonic anhydrase enzyme is immobilized on a hollow fiber surface of the primary membrane gas absorber;
carbonic anhydrase enzyme immobilized on a hollow fiber surface of the primary membrane gas absorber;
an immobilization support on the hollow fiber surface of the primary membrane gas absorber, the immobilization support comprising diatom algae silica;
a first RACR-PBR configured to cultivate a filamentous, haloalkaliphilic cyanobacterium;
a second RACR-PBR configured to cultivate a filamentous, haloalkaliphilic microalgae;
a third RACR-PBR configured to cultivate a non-haloalkaliphilic microalgae;
a lignocellulosic biomass pathway configured to produce at least one of biogas, bio-oil, and bio-char;
a waste pathway configured to recover nitrogen and phosphorous from fractionated wastewater;
at least one of a non-thermal plasma reactor, a dielectric barrier discharge reactor, a soda ash absorber, a hydrothermal liquefaction process unit, and a hydrotreatment reactor; and
a growth medium circulating between the primary membrane gas absorber and the at least one runway algal cassette reactor-photobioreactor, wherein the primary membrane gas absorber is configured to receive the enrichment medium from the at least one runway algal cassette reactor-photobioreactor in a bicarbonate-depleted state, and the at least one runway algal cassette reactor-photobioreactor is configured to receive the growth medium in a bicarbonate-enriched state.

20. The bioproduct manufacturing system of claim 19, wherein:
   the first RACR-PBR comprises the filamentous, haloalkaliphilic cyanobacterium,
   the second RACR-PBR comprises the filamentous, haloalkaliphilic microalgae, and
   the third RACR-PBR comprises the non-haloalkaliphilic microalgae.

* * * * *